(12) United States Patent
Shimizu

(10) Patent No.: US 6,275,777 B1
(45) Date of Patent: Aug. 14, 2001

(54) SCANNING CYTOMETER

(75) Inventor: Kotaro Shimizu, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/178,986

(22) Filed: Oct. 26, 1998

(30) Foreign Application Priority Data

Oct. 28, 1997 (JP) .................................................. 9-295533

(51) Int. Cl.[7] ............................ G01N 31/00; G06F 17/18; G06K 9/00
(52) U.S. Cl. .............................. 702/30; 702/32; 702/179; 382/133
(58) Field of Search ............................ 702/19–23, 25–27, 702/29–32, 85, 86, 100, 155, 159, 179, 180, 183–185, 189, 193; 382/133, 134

(56) References Cited

U.S. PATENT DOCUMENTS

| 3,873,974 | * | 3/1975 | Bouton et al. | 382/134 |
|---|---|---|---|---|
| 5,072,382 | | 12/1991 | Kamentsky | 382/133 |
| 5,317,162 | * | 5/1994 | Pinsky et al. | 250/461.2 |
| 5,856,665 | * | 1/1999 | Price et al. | 250/205 |
| 5,885,840 | * | 3/1999 | Kamentsky et al. | 436/63 |
| 6,148,096 | * | 11/2000 | Pressman et al. | 382/133 |
| 6,181,811 | * | 1/2001 | Kuan et al. | 382/133 |

FOREIGN PATENT DOCUMENTS 3-255365  11/1991 (JP).

* cited by examiner

Primary Examiner—Patrick Assouad
Assistant Examiner—Manuel L. Barbee
(74) Attorney, Agent, or Firm—Frishauf, Holtz, Goodman, Langer & Chick, P.C.

(57) ABSTRACT

Initial values including measurement conditions are set at pre-measurement executed prior to main measurement. An area on a sample of a cell population wider than that for the main measurement is two-dimensionally scanned at a high speed in accordance with the set initial values to acquire statistic data of the cell population. Measurement conditions used for the main measurement are determined based on the acquired statistic data.

7 Claims, 16 Drawing Sheets

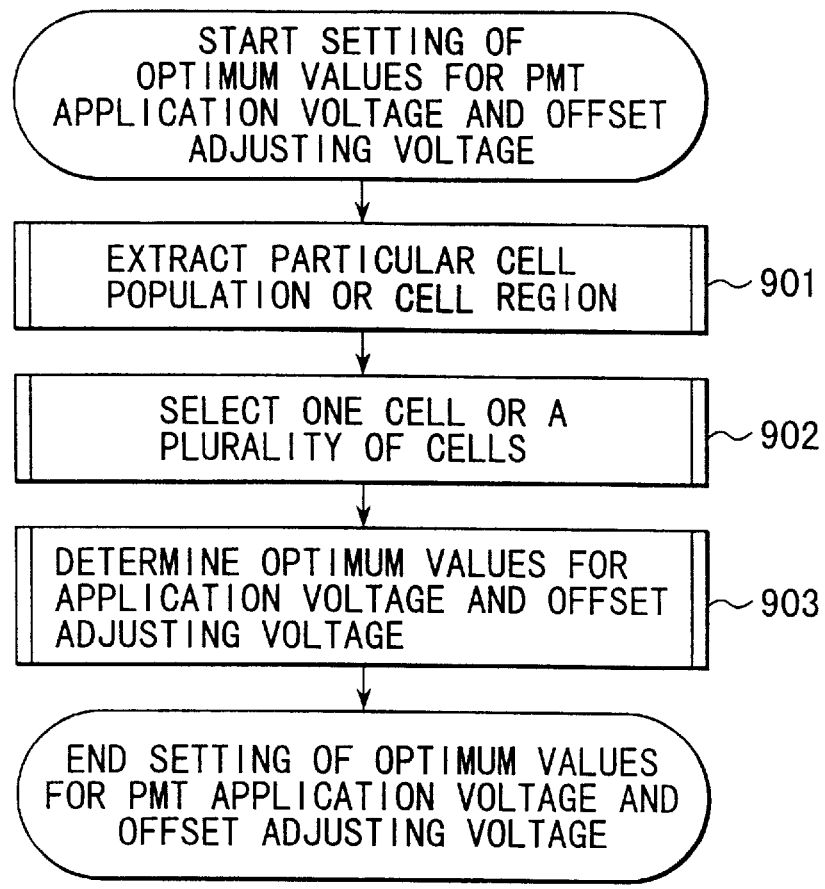
FIG. 11A
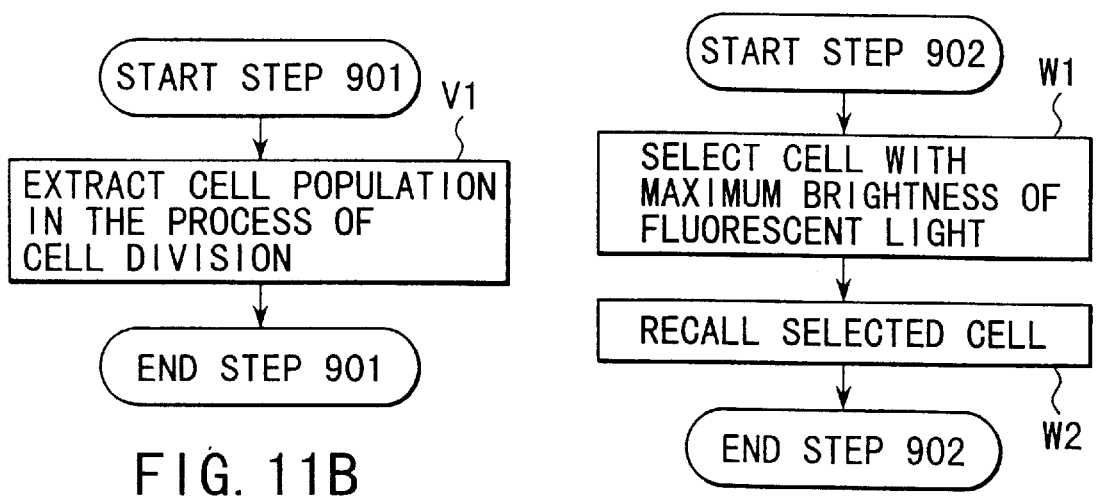
FIG. 11B
FIG. 11C

SCANNING CYTOMETER

BACKGROUND OF THE INVENTION

The present invention relates to a scanning cytometer for acquiring cytometric data of a cell population as a sample by scanning and measuring the cell population with optical beams in accordance with measuring conditions such as a measuring range and measuring speed for the sample.

There have been flow cytometers which are apparatuses for irradiating individual cells in a cell population of a living organism biochemically identified by a fluorescent pigment with a laser to form laser spots where the cells are excited to emit fluorescent or scattered light, measuring the light at a high speed and analyzing the results of the measurement to acquire and present statistic data as cytometric data representing the immunological, genetic and proliferative characteristics of the cell population.

The laser of such a flow cytometer and spots formed by converging laser beams therefrom are fixed. Cells are measured on such fixed spots using converged beams by causing the cells to flow through the spots along with a jetted stream of water in a state in which the individual cells are floating apart from each other in a drifting liquid. With such a method of measurement, it is not possible to find the cell associated with a particular item of data to observe the state of the cell and to identify measurement the data associated with each cell after the measurement.

An alternative to such flow cytometers, scanning cytometers have been developed including the invention disclosed in Jpn. Pat. Appln. KOKAI Publication No. 3-255365 titled "Method and Apparatus for Measuring a Plurality of Optical Characteristics of Living Sample" wherein spots formed by converged laser beams are scanned across a cell population on a slide glass to detect fluorescent and scattered light emitted by individual cells in the cell population and wherein resultant data are processed.

In such a scanning cytometer, scanning is performed with a scanner driven in accordance with a scanning waveform, etc. which deflects laser beams, e.g., a focused spot at X-direction and moves a moving scanning stage at Y-direction to scan a cell population on the slide glass on a moving scanning stage. Fluorescent and scattered light emitted by cells excited by the laser beams as spots is converted into electrical signals which are collected in accordance the logic of a data input signal output along with the scanner scanning waveform.

A scanning cytometer processes images formed as a result of scanning, extracts measurement data on each cell such as the sum of the values of fluorescent light, area of the cell, the maximum value of fluorescent light, coordinates on the scanning stage, elapse time since the beginning of the measurement, the distance of the cell to the nearest cell, the circumference of the cell and the number of spots in the cell and processes such data statistically to provide the results to the measuring personnel (operator) through an interface such as a computer.

Since a tremendous number of cells are processed resulting in a very wide measuring area, it is not possible to collect such data at a time. Therefore, the measuring area is divided into small ranges referred to as "strips", and measurement is performed on each of such strips.

Scanning cytometers are significantly different from flow cytometers in that they have a function referred to as "recall function" which makes it possible to retrieve each cell of interest from statistic data obtained as described above.

When measurement is carried out using a scanning cytometer, it is necessary to set measuring conditions prior to the measurement. The measuring conditions e.g., a voltage applied by a photomultiplier (PMT) for converting fluorescent light emitted by cells into electrical signals and an offset adjusting voltage of the photomultiplier, the gain and the offset for a photodiode (PD) as a detector for converting scattered light into electrical signals, the measuring area, contouring threshold and minimum cell area.

Those measuring conditions are basically set by the operator at values which are desired or determined as appropriate by the operator.

A description will now be made with reference to FIGS. 1A and 1B on how to set, for example, the application voltage of the PMT of a conventional scanning cytometer and the offset adjusting voltage of the same. There are two methods to set the application voltage and offset adjusting voltage of the PMT.

As shown in FIG. 1A, the first method is to obtain a fluorescent image for one strip by performing measurement with the application voltage and offset adjusting voltage of the PMT set at appropriate initial values. The resultant fluorescent image of a cell is examined to obtain the brightness of the fluorescent light emitted by the cell and the brightness of the background and, if the brightness is not a proper value or is out of a proper range, the application voltage and offset adjusting voltage of the PMT are reset according to the judgment of the operator. An optimum value is determined after repeating such measurement, judgment and resetting several times.

As shown in FIG. 1B, the second method is to scan a single line and to perform a photometric process with the application voltage and offset adjusting voltage of the PMT set at appropriate initial values by only deflecting laser beams projected upon an arbitrary cell population without moving the scanning stage. The result of the photometric process can be presented to the operator real time. The operator adjusts the application voltage and offset adjusting voltage of the PMT by trial and error based on the result of photometry such that the brightness of fluorescent light emitted by the cells and the brightness of the background assume appropriate values or stay within appropriate ranges.

A description will now be made with reference to FIGS. 2A and 2B on methods for setting the measuring area of a conventional scanning cytometer. There are two methods for setting the measuring area.

As shown in FIG. 2A, according to the first method, the operator directly inputs the values of the coordinates of the starting and end points of measurement on a computer.

As shown in FIG. 2B, according to the second method, the operator moves the scanning stage while observing the sample, stops the scanning stage at an appropriate position and specifies the location (point) to start measurement. Then, the operator moves the scanning stage again while observing the sample, stops the scanning stage at an appropriate position and specifies the location (point) to end the measurement.

Two problems arise as described below when the application voltage and offset adjusting voltage of the PMT are set in a conventional scanning cytometer.

The first problem is wasteful time and labor spent by the operator during condition setting repeated several times by trial and error.

The second problem arises in that there is no assurance that conditions for measurement are appropriate in obtaining data for cells in a wide area in actual measurement because the measurement conditions are set based on brightness data of cells or a cell population in a range as small as one strip or one line. Specifically, let us assume that the cell cycle of a cell in the process of cell division is actually measured on a single line scan with the application voltage and offset adjusting voltage of the PMT set at appropriate values for a cell in a stable state. A cell in the process of cell division emits a greater amount of fluorescent light than a cell in a stable state because of a difference in the amount of DNA. As a result, when the cell in the process of cell division is measured with the application voltage and offset adjusting voltage of the PMT set at appropriate values for the cell in a stable state, the brightness of fluorescent light from the cell in the process of cell division can exceed the measuring area. Measurement must be redone when the measuring area is exceeded.

Although the first problem can be solved by an existing process of automatically adjusting the application voltage and offset adjusting voltage of a PMT employed in industrial scanning microscopes or scanning microscopes for living organisms, the second problem remains unsolved.

Even if the existing process for automatically adjusting the application voltage and offset adjusting voltage of a PMT is applied to an actual measuring area instead of a small area such as one strip or one line to solve the second problem, another problem arises in that a long time is spent for setting conditions because the area is widened.

A problem occurs as described below when a measuring area is set for a conventional scanning cytometer depending on how the operator sets the measuring area on the sample. A sample observed on a scanning cytometer is a population of cells colored with a fluorescent pigment such as a smear of floating cell sap or a touch smear of organic cells placed on a slide glass which is manually prepared. The cells can be unevenly distributed on the slide glass or variation can occur in fluorescent coloring depending on the manner in which the sample is prepared.

During the measurement of such a sample, the efficiency of cell measurement and the accuracy of measurement and analysis can be reduced when the measuring area is set based on subjective judgment of the operator as in the prior art.

The reason is that the operator can not know the state of distribution of a cell population across a wide area on the slide glass and the degree of the uniformity of fluorescent coloring in a conventional scanning cytometer. It can happen that a region including a small number of cells, a region where an agglomeration of cells is formed, or a region having variation of fluorescent coloring is set as the measuring area. The efficiency of measurement is reduced if a region including a small number of cells is measured. The measuring efficiency is also reduced in a region where cells concentrate so densely that a cell agglomeration is formed. When a region having variation of fluorescent coloring is measured, the. distribution of the sum of values of fluorescent light from individual cells can be dependent not only on the amount of cellular components such as DNA but also on variation of fluorescent coloring, and the result of measurement and analysis using a cytometer includes artifacts that are attributable to the dependence on the variation of fluorescent coloring.

Attempts to obtain quantitative knowledge of the state of distribution of a cell population across a wide area and the degree of uniformity of fluorescent coloring will not be practical because such measurement over a wide area will take an enormous amount of time if it will be carried out similarly to normal measurement.

It is an object of the present invention to provide a scanning cytometer in which conditions for measurement such as a gain and an offset of a detector and a measuring area can be automatically set based on cell data in a wide area.

BRIEF SUMMARY OF THE INVENTION

The above-described object is achieved by a scanning cytometer for scanning a cell population as a sample with optical beams in accordance with conditions for measurement and for measuring light from the cells in the cell population with detectors to acquire cytometric data of the cell population, comprising:

means for providing main measurement in accordance with main measurement conditions as measurement conditions and pre-measurement performed prior to the main measurement in accordance with initial values for pre-measurement including measurement conditions;

setting means for setting the initial values for pre-measurement;

execution means for acquiring statistic data of the cell population by performing two-dimensional scanning of the cell population across an area wider than the area for the main measurement at a rate higher than the rate of the main measurement with optical beams in accordance with the initial values for pre-measurement set by the setting means; and determination means for determining the main measurement conditions based on the statistic data acquired by the execution means.

In such a scanning cytometer, the measurement conditions for main measurement can be determined based on the result of the pre-measurement executed prior to the main measurement. In addition, since an area wider than the main measurement range is measured at a rate higher than the rate of the main measurement during the pre-measurement, the measurement conditions determined by the result of the pre-measurement are highly accurate in spite of the fact that they are acquired in a short period of time.

The measurement conditions include the control voltages as the control conditions of the detectors a measuring area, a contouring threshold and a minimum cell area. The detectors include a photomultiplier for detecting fluorescent light from cells and a photodiode for detecting scattered light from cells. The control voltages include the application voltage and offset adjusting voltage of the photomultiplier and the gain and the offset of the photodiode.

The contouring threshold and minimum cell area are conditions to be satisfied to carry out cell extraction and are normally manually set by the operator. The contouring threshold is a threshold for dividing the background and a cell region.

Cell extraction is to extract a cell region or a region recognized as a cell from data of a scanned image reconstructed on a two-dimensional plane based on optical information from the sample detected by the photodetectors (PD) using brightness as optical intensity.

The contouring threshold is related to a minimum appropriate value of brightness KTmin of brightness data K for determining optimum values for the application voltage and offset voltage of the PMT and the gain and the offset of the PD. Specifically, the minimum appropriate value of brightness KTmin is set such that it does not exceed the contouring threshold. If the minimum appropriate value of brightness KTmin exceeds the contouring threshold, the background can be recognized as a cell. To put this conversely, the contouring threshold may be determined such that it exceeds the minimum appropriate value of brightness KTmin.

Referring to the minimum cell area, when this value is too small, background noises or foreign substances can be regarded as cells. When it is too great, recognition misses cells that are required. It is therefore idealistic to determine the optimum value depending on the types of samples.

The following method is employed to obtain measurement conditions for a scanning cytometer which acquires cytometric data of a cell population as a sample by scanning it with optical beams according to the measurement conditions and by measuring light from the cells in the cell population with detectors. The method comprises the steps of:

providing main measurement in accordance with main measurement conditions as measurement conditions and pre-measurement performed prior to the main measurement in accordance with initial values for pre-measurement including measurement conditions;

setting the initial values for pre-measurement;

acquiring statistic data of the cell population by performing two-dimensional scanning of the cell population across an area wider than the area of the main measurement at a rate higher than the rate of the main measurement with optical beams in accordance with the initial values for pre-measurement set by the setting means; and determination means for determining the main measurement conditions based on the statistic data acquired by the execution means.

The above-described object is achieved with a scanning cytometer as described below. The scanning cytometer which acquires cytometric data of a cell population as a sample by scanning it with optical beams according to conditions for measurement and by measuring light from the cells in the cell population with detectors, comprises:

Providing means for providing main measurement in accordance with conditions for main measurement and pre-measurement performed prior to the main measurement in accordance with conditions for pre-measurement;

setting means for setting at least one of conditions for the control conditions of the detector, the measuring area, the contouring threshold and minimum cell area;

execution means for acquiring statistic data of the cell population by performing two-dimensional scanning of the cell population across an area wider than the area for the main measurement at a rate higher than the rate of the main measurement with optical beams in accordance with initial values based on the conditions set by the setting means; and determination means for determining the conditions for main measurement based on the statistic data acquired by the execution means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 11A to 11D are flow charts showing steps required for determining optimum values for the application voltage and the offset adjusting voltage of the PMT according to the second embodiment of the present invention;

DETAILED DESCRIPTION OF THE INVENTION (First Embodiment)

A first embodiment of the present invention will now be described with reference to the accompanying drawings.

Figure 1A:
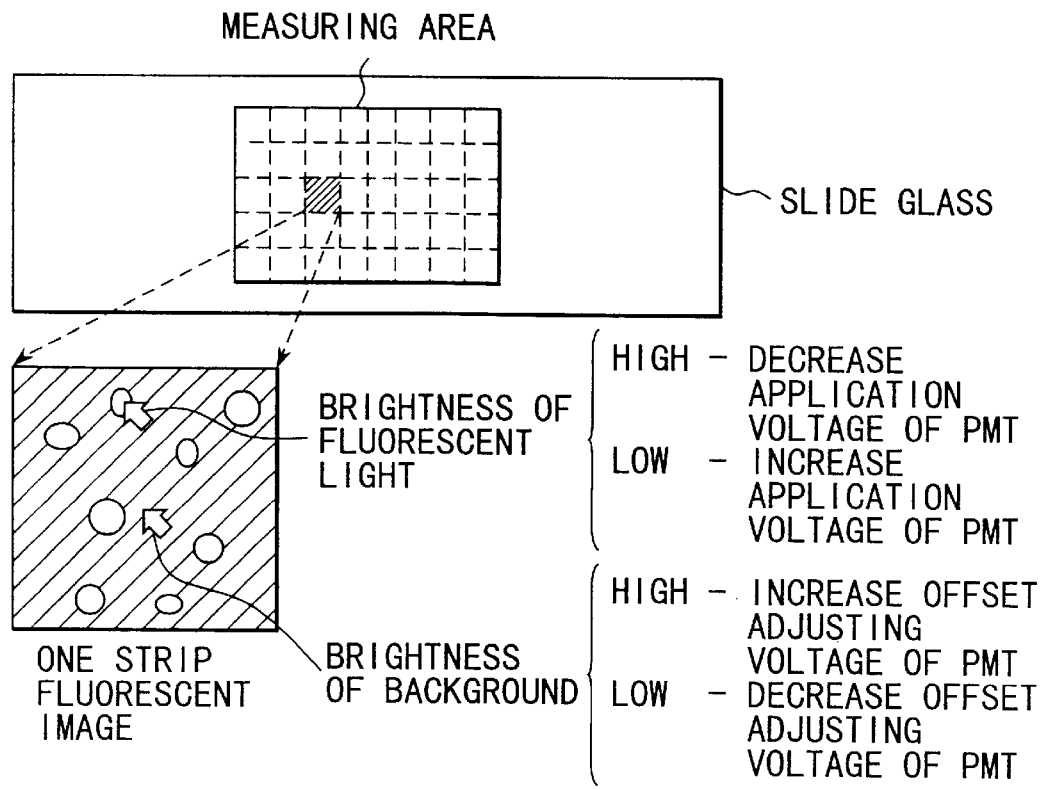
FIGS. 1A and 1B illustrate methods of setting an application voltage and an offset adjusting voltage of a PMT of a conventional scanning cytometer.
Figure 1B:
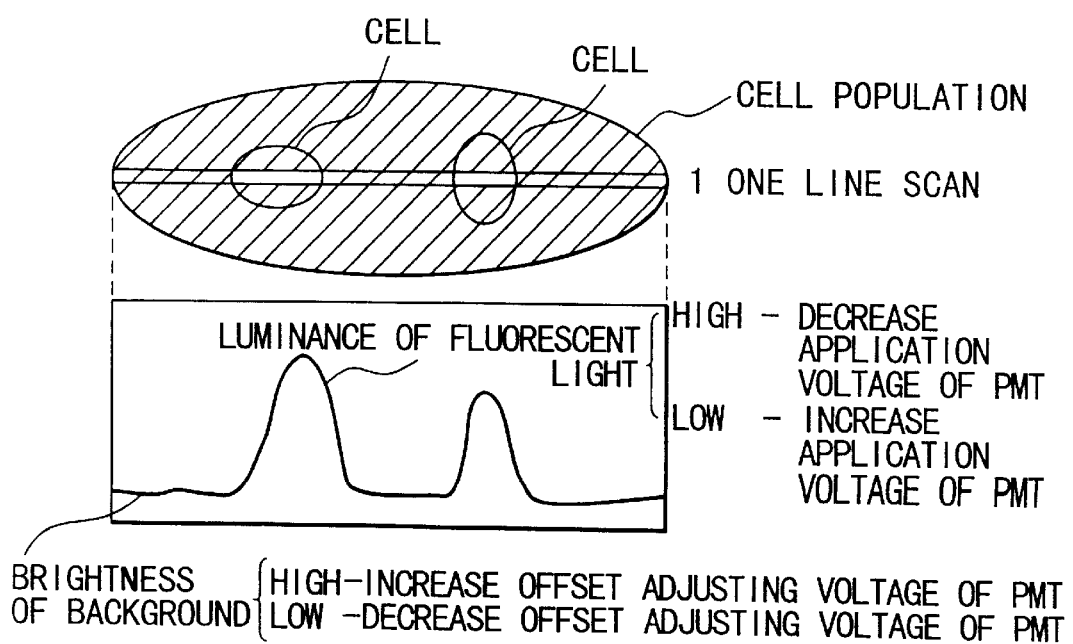
Figure 2A:
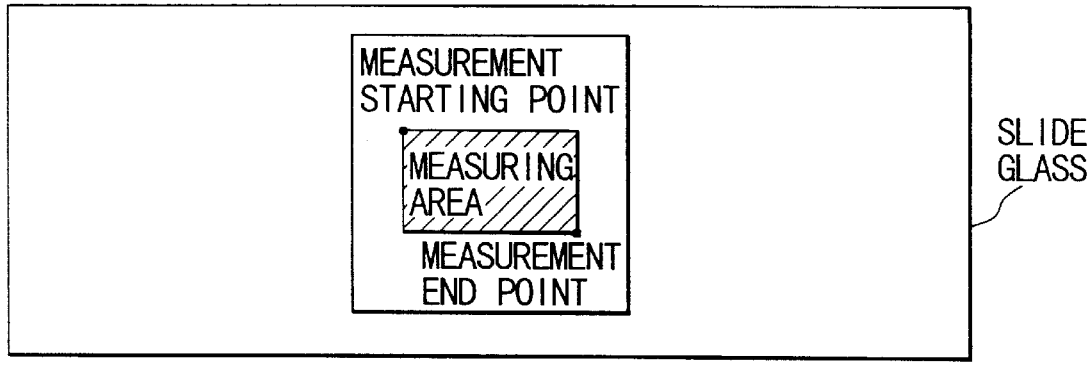
FIGS. 2A and 2B illustrate methods of setting a measuring area of a conventional scanning cytometer.
Figure 2B:
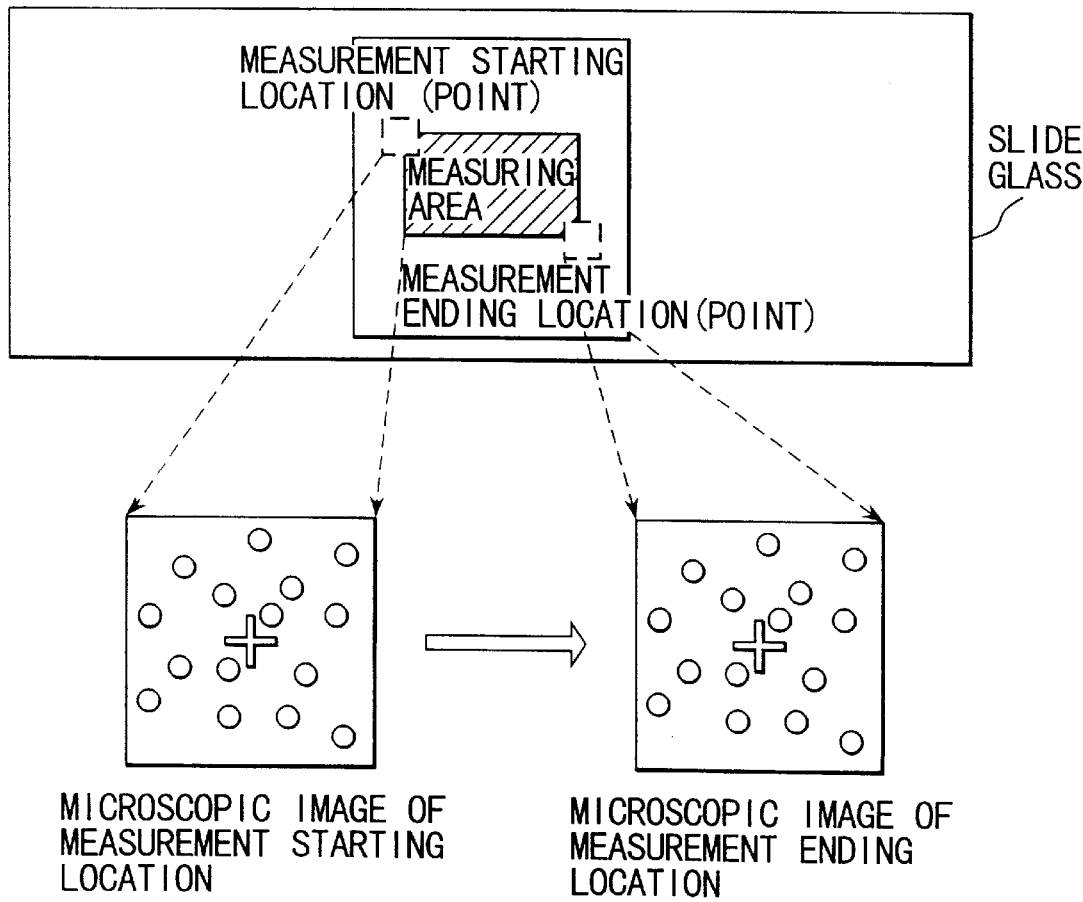
Figure 3:
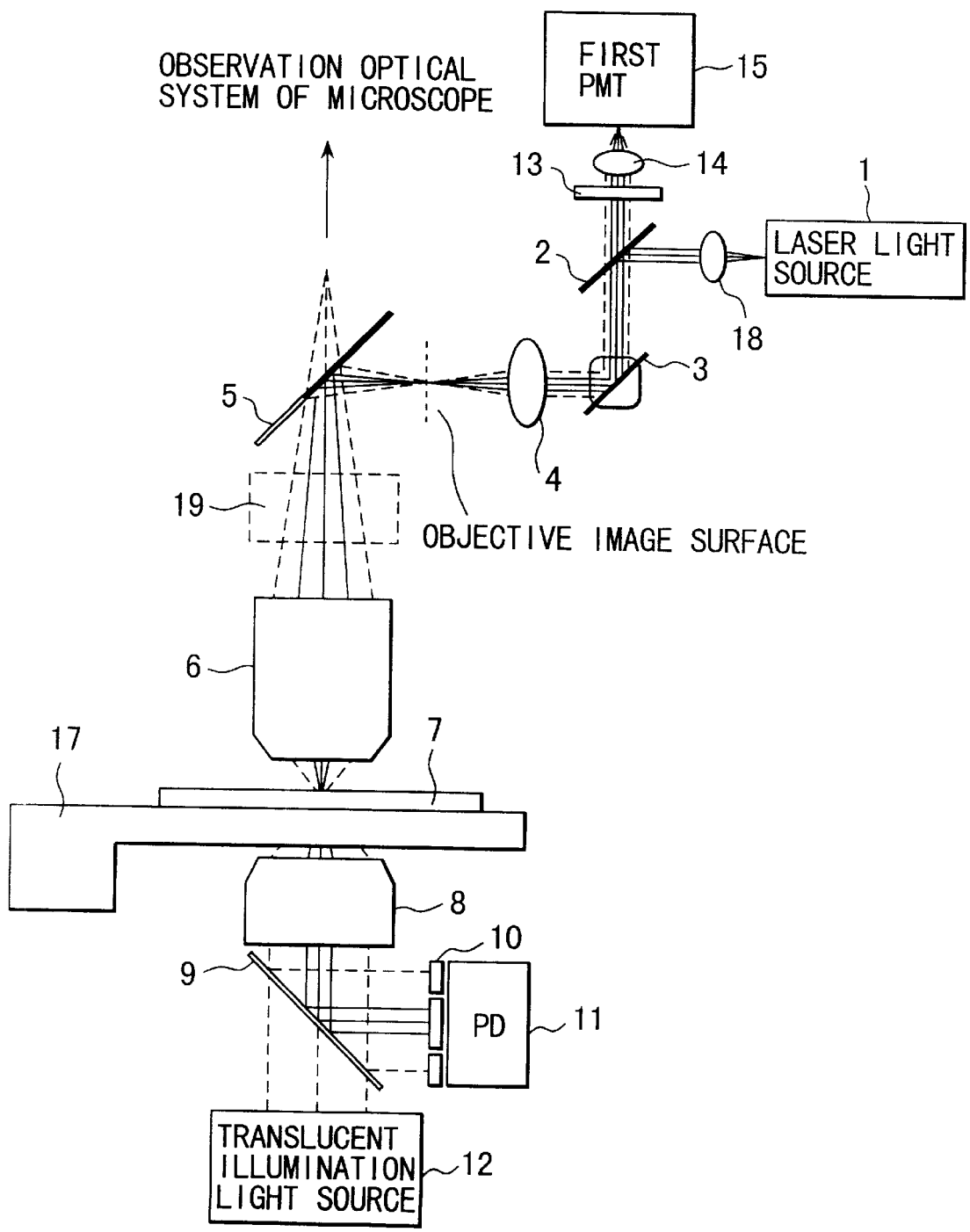
FIG. 3 is a schematic illustration of mechanical and optical configurations of a scanning cytometer according to a first embodiment of the present invention.

FIG. 3 illustrates mechanical and optical configurations of a scanning cytometer according to the present embodiment. Referring to FIG. 3, laser beams emitted by a laser light source 1 are appropriately converged by a spot projection lens 18, reflected thereafter by a dichroic mirror 2, reflected further by a galvano-mirror 3 which rotates about an axis of rotation perpendicular to the plane of the drawing, focused thereafter by an iris projection lens 4 upon an objective image surface to form an image thereon and then impinge upon a light path switching mirror 5. Thus, the intervention of the rotating galvano-mirror 3 causes the laser beams to be scanned up and down on the plane of the drawing in the position of the light path switching mirror 5.

The laser beams are reflected by the light path switching mirror 5 and thereafter impinge upon an objective lens 6 to be focused on a sample 7 to form an image thereon. Thus, the laser beam spot formed on the sample 7 is scanned to the left and right on the plane of the drawing. The surface of the sample 7 is two-dimensionally scanned by the laser spot by scanning the laser beams with the galvano-mirror 3 as optical deflecting means to the left and right on a sample plane of the drawing and by moving a scanning stage 17 in a direction perpendicular to the plane of the drawing simultaneously.

A fluorescent pigment biochemically marked on cells on the sample 7 in advance is excited by the laser beams (laser spot) to emit fluorescent light.

The fluorescent light from the sample 7 travels backward along the above-described light path through the objective lens 6, light path switching mirror 5, iris projection lens 4 and galvano-mirror 3 to pass upward through the dichroic mirror 2. The fluorescent light that has passed through the dichroic mirror 2 passes through a barrier filter 13 to be collected by a collective lens 14 on to a light receiving surface of a photomultiplier (PMT) 15.

Light scattered by the cells on the sample 7 is collected by a condenser lens 8 along light which has downwardly passed through the sample 7, reflected by a beam splitter 9 and thereafter enter a ring slit 10. The ring slit 10 blocks the light transmitted through the sample 7 and allows only the scattered light to pass therethrough to be incident upon a light receiving surface of a photodiode (PD) 11.

In the scanning cytometer having the above-described mechanical and optical configurations, the sample 7 is two-dimensionally scanned with the laser spot; fluorescent light from the sample 7 is detected by the photomultiplier 15; and scattered light from the sample 7 is detected by the photodiode 11.

While FIG. 3 shows the use of only one kind of fluorescent pigment, fluorescent beams of light having different wavelengths from a plurality of fluorescent pigments can be simultaneously detected by increasing the numbers of the dichroic mirror 2, barrier filter 13, collective lens 14 and PMT 15.

The light path switching mirror 5 is removably provided in the light path of laser beams, and an image of the sample 7 can be formed on a microscope observation system 16 by removing the light path switching mirror 5 from the light path. That is, the scanning cytometer according to the present invention is formed by a unit for acquiring cytometric data and a microscope unit which are integral with each other. Further, a recall function is added to allow reference on a cell of interest from the unit to acquire cytometric data to the microscope unit or from the microscope unit to the unit to acquire cytometric data and cross reference between the unit to acquire cytometric data and the microscope unit.

The microscope unit can be used as a normal microscope by using illumination with a translucent illumination light source 12 or a downward illumination light source 19. As a result, the operator can observe a transmitted image or fluorescent image of the sample 7 with the microscope or can perform microscopic photographing with a CCD camera or photographic device.

An electrical configuration of the above-described scanning cytometer will be described with reference to FIG. 4.

Figure 4:
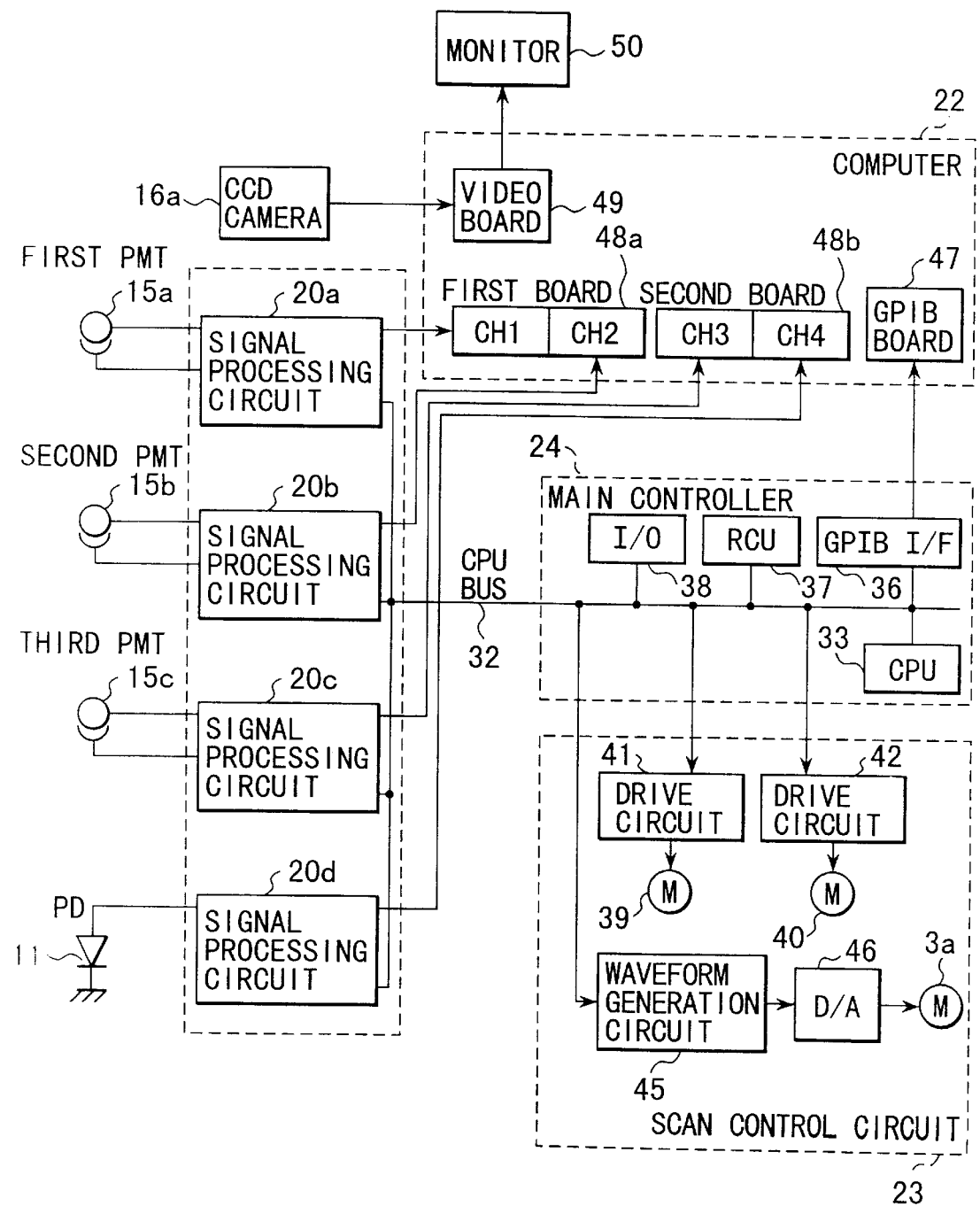
FIG. 4 is a block diagram showing an electrical configuration of the scanning cytometer of the first embodiment of the present invention.

As shown in FIG. 4, the circuit configuration incorporated in the scanning cytometer described here comprises three signal processing circuits 20a, 20b and 20c for converting electrical signals associated with respective intensity of fluorescent light acquired by three PMTs, i.e., first, second and third PMTs 15a, 15b and 15c into image data, a signal processing circuit 20d for converting an electrical signal associated with the intensity of scattered light acquired by the PD 11 into image data, a computer 22 for processing the image data provided by the signal processing circuits 20a to 20d to generate a scanned image and a processed image, a scan control circuit 23 for two-dimensionally scanning the sample 7 with a laser spot and a main controller 24 for controlling the operation of the signal processing circuits 20a to 20d and the scan control circuit 23.

The signal processing circuit 20a has a circuit for changing a applied voltage and an offset adjusting voltage of the first PMT 15a. A CPU 33 controls the applied voltage and the offset adjusting voltage through a CPU bus 32 and above the circuit of the signal processing circuit 20a.

The signal processing circuits 20b and 20c corresponding to the second and third PMTs 15b and 15c are the same as the signal processing circuit 20a.

The signal processing circuit 20d has a circuit for changing a gain and an offset of the PD 11.

The CPU 33 controls the gain and the offset through the CPU bus 32 and above the circuit of the signal processing circuit 20d.

A description will now be made on detailed circuit configurations of the main controller 24 and scan control circuit 23.

Connected to the CPU bus 32 of the main controller 24 are a GPIB (general purpose interface bus) interface control circuit 36 for various types of communication between the CPU 33 and computer 22, an RCU (remote control unit) 37 which are a group of switches for controlling the movement of the scanning stage 17 and an input/output (I/O) circuit 38. Further, drive circuits 41 and 42 for two stepping motors (M) 39 and 40 for moving the scanning stage 17 in X- and Y-directions and a waveform generation circuit 45 for forming a waveform for driving a motor 3a of the galvano-mirror 3 are connected to the CPU bus 32. The waveform generated by the waveform generation circuit 45 is applied through a D/A converter 46 to the motor 3a of the galvano-mirror 3 which is driven and controlled by the applied voltage.

Therefore, the main controller 24 can control the operation of the scanning stage 17 and galvano-mirror 3 through the scan control circuit 23 to dimensionally scan the sample 7 with a laser spot in an arbitrary manner.

Further, the RCU 37 includes a four-direction (up, down, left and right) key. As the operator presses the direction key, the CPU 33 is informed of the operation and issues an instruction to the stepping motor drive circuits 41 and 42 in accordance with the informed operation to move the scanning stage 17. When the movement of the scanning stage 17 is finished, the movement is informed to the computer 22 through the GPIB interface control circuit 36.

Thus, the operator can freely operate the scanning stage 17 through the RCU 37, and the computer 22 can be notified of the termination of the operation of the scanning stage 17 by the operator.

A circuit configuration of the computer 22 will now be described in detail.

The computer 22 includes a GPIB board 47 for controlling the GPIB and can communicate with the CPU 33 of the main controller 24 through the GPIB interface control circuit 36 of the main controller 24. Therefore, the computer 22 can perform control over operations such as the starting and termination of the operation of the stage 17 and galvano-mirror 3 through the main controller 24. When the scanning stage 17 is moved using the RCU 37 as described above, the computer 22 can be notified of such from the main controller 24.

Expansion slots of the computer 22 used in the scanning cytometer described here accept two memory boards, i.e., first and second memory boards 48a and 48b, one GPIB board 47 as described above and one video board 49.

Memory circuits that support two channels are mounted on each of the memory boards 48a and 48b. As illustrated, data transferred from the signal processing circuit 20a is input to the memory circuit for a channel 1 (CH 1) on one of the memory board 48a, whereas data transferred from the signal processing circuit 20b is input to the memory circuit for a channel 2 (CH 2). Further, data transferred from the signal processing circuit 20c is input to the memory circuit for a channel 3 (CH 3) on the other memory board 48b, whereas data transferred from the signal processing circuit 20d is input to the memory circuit for a channel 4 (CH 4).

Each of the channels on the memory boards 48a and 48b is formed by two memory banks, so that while data is being transferred to one of the memory banks from the signal processing circuit 20a, the computer 22 can access the other memory bank.

The CCD camera 16a is mounted on the microscope to allow a transmitted image or fluorescent image of a sample to be observed. A video signal from the CCD camera 16a is input to the video board 49 of the computer 22 and is synthesized with a graphic image in the computer 22 to be displayed on a monitor 50. The synthesized microscope image can be displayed in real time, and computer graphics can be overlaid on the microscope image.

A microscope image displayed on the computer 22 is divided into pixels as much as 640×480 dots, and measurement is made in advance to obtain a coordinate value in the coordinate system for the movement of the stage which represents the size of each pixel on the screen in $\mu$m in the coordinate system. Since coordinate data of the position of each cell is in the coordinate system on the scanning stage 17, a converted coordinate value can be converted into a coordinate value on a microscope image. Referring to the method for measuring a converted coordinate value, a certain target image is displayed on the microscope screen; the target image is selected and the coordinate thereof on the screen is identified; the scanning stage 17 is moved by an amount in the range of the movement of the target in the screen; and the target image is selected again to calculate the ratio between the amount of the movement on the screen and the amount of the actual movement of the scanning screen 17.

The positional relationship between the scanning stage 17 and the microscope image is determined by aligning the optical axis of the objective lens 6 shown in FIG. 3 with the center of the microscope image. The objective lens 6 shown in FIG. 3 is replaceable and has a variable magnification factor. Since a converted coordinate value as described above depends on the magnification factor of the objective lens 6 actually used, the magnification factors of each of replaceable objective lenses 6 are stored in the computer 22. When the magnification factor of the objective lens 6 is changed, the moving speed of the scanning stage 17 is automatically switched.

The basic software used in the computer 22 is software which is capable of displaying rectangular display areas of the monitor 50 in any size referred to as windows on the display screen and displaying statistic graphs of cell data and real time images from the CCD camera 16a in the windows. All kinds of application software on the computer 22 that control the present apparatus can be activated on the basic software.

A description will now be made with reference to FIGS. 5 to 7 on a procedure for setting measurement conditions for the scanning cytometer according to the present embodiment.

Figure 5:
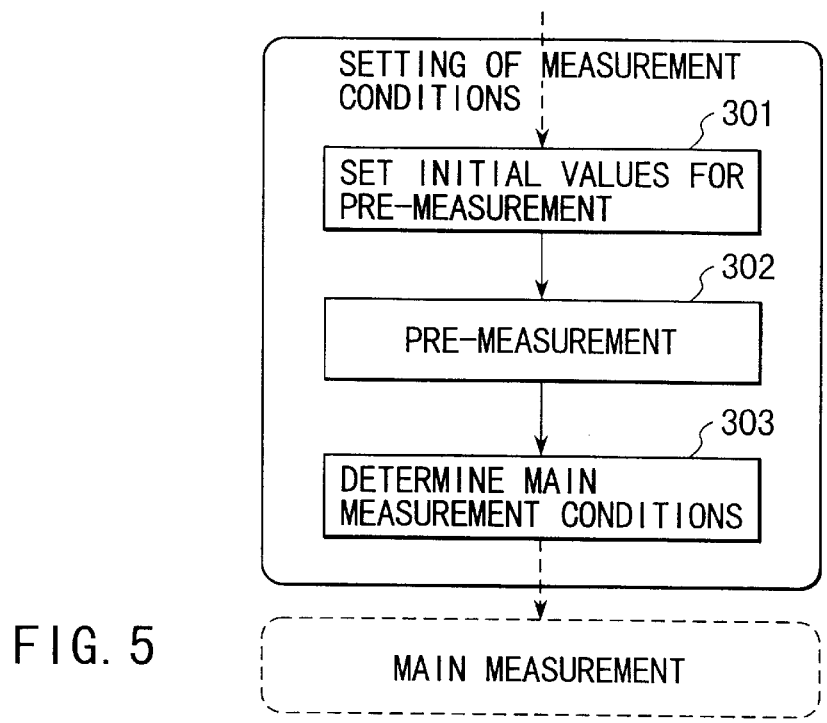
FIG. 5 is a flow chart illustrating means for setting measurement conditions according to the first embodiment of the present invention.

As shown in FIG. 5, the setting of measurement conditions carried out prior to main measurement comprises three steps, i.e., the setting of initial values including measurement conditions for pre-measurement (step 301), the execution of the pre-measurement (step 302) and the determination of main measurement conditions as measurement conditions (step 303).

Referring first to the setting of the pre-measurement conditions (step 301), initial values of conditions required for the execution of the pre-measurement (step 302) including measurement conditions are set. The initial values set here may be values stored in advance in a memory of the computer 22 or values desired by the operator and set using the computer 22 or values determined by a series of predetermined processes.

Next, an objective lens 6 having a low magnification factor is selected, and pre-measurement is carried out on a cell population as a whole distributed on a slide glass or on a cell population included in a range which is at least wider than the measuring area for the main measurement (step 302).

Figure 6:
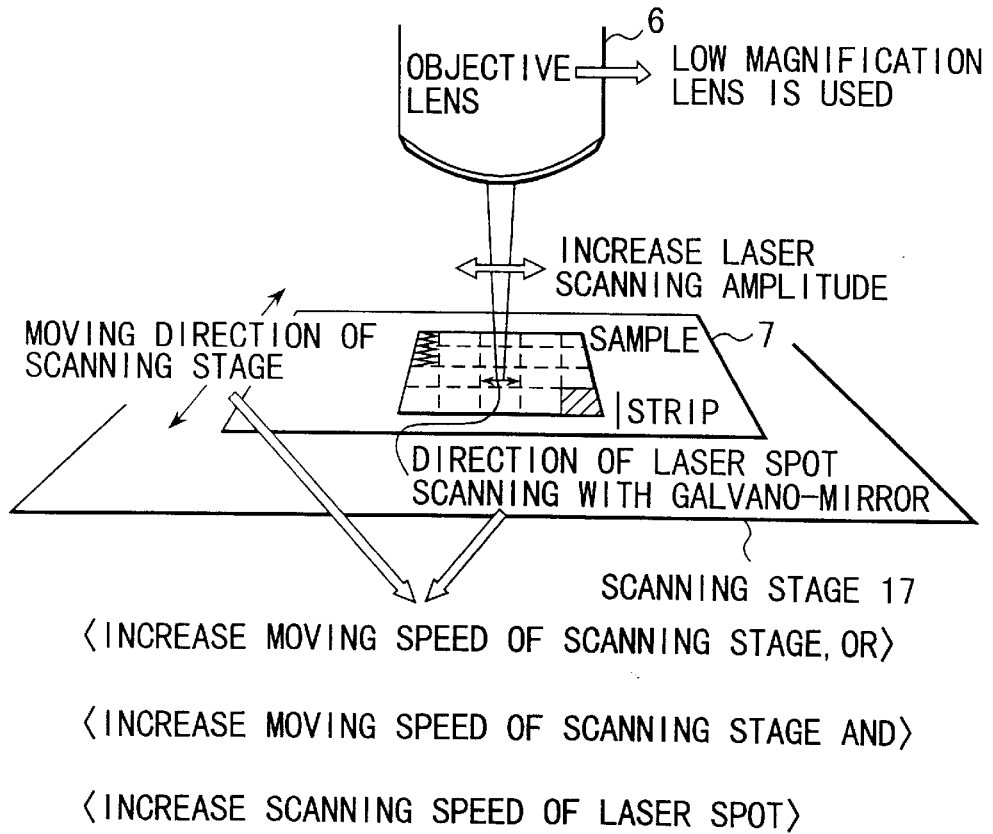
FIG. 6 illustrates rough scan according to the first embodiment of the present invention.
Figure 7:
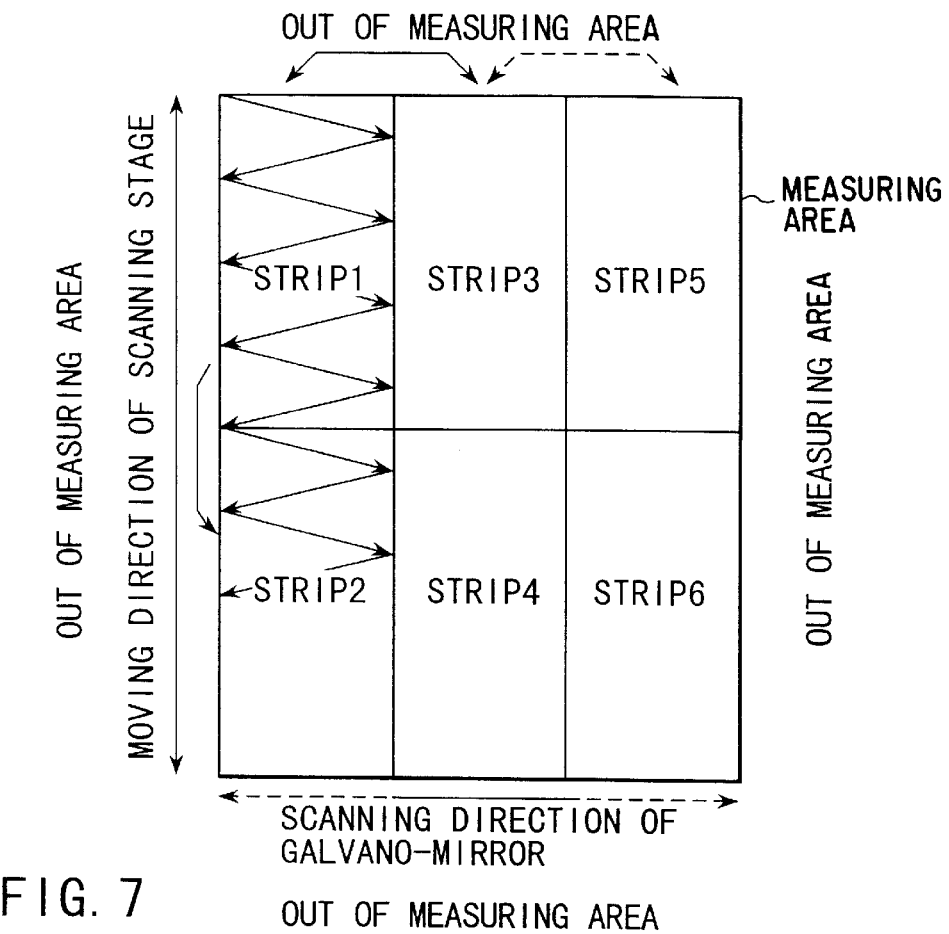
FIG. 7 illustrates a method for dividing a measuring area into strips and scanning the same according to the first embodiment of the present invention.

When the execution of the pre-measurement (step 302) is started, as shown in FIG. 6, the sample 7 is scanned with a laser spot on the basis of two dimensions defined by the rotation of the galvano-meter 3 in the X direction and the movement of the scanning stage 17 in the Y direction. The measuring area is divided into several strips because of a limitation placed by the area that the galvano-meter 3 can scan and a limitation on the size of scanned image data that can be collected at a time attributable to the capacity of the bank memories. As shown in FIG. 7, when a strip 1 is finished, for example, the scanning sequentially proceeds to a strip 2.

While the sample 7 is subjected to two-dimensional scan with laser spots, the amount of fluorescent light emitted by cells with fluorescent coloring is detected by the PMTs 15a to 15c and, if necessary, the amount of scattered light therefrom is also detected by the photodiode 11 to generate scanned image data through the signal processing circuits 20 (20a to 20d).

Thereafter, thresholding is performed to extract cell regions from the scanned image data, and characterizing quantities are calculated as cell data for each of the extracted cell regions, the characterizing quantities including the sum of the values of fluorescent light, the area, the maximum value of fluorescent light, the coordinate on the scanning stage of each cell, the distance of each cell from the nearest cell (distance between nearest cells), the circumference, the number of spots in the cell, the luminance of background around each cell and the like. It is determined from the resultant cell data whether a cell of interest is a cell formed by a plurality of cells recognized as a single entity (multiple cell). Such a cell can be eliminated during or after the measurement. Referring to how to discriminate a multiple cell, the coordinate in the cell region of interest which exhibits the maximum luminance is identified. Then, image data is traced from the coordinate having the maximum value in eight directions within a rectangle surrounding the cell region. If there is any trace line including a peak at a coordinate other than the coordinate of the maximum value, the region is regarded as a multiple cell.

The data of each cell thus acquired is automatically stored in the memory of the computer 22 and can be thereafter treated as statistic data.

An objective lens 6 having a low magnification factor is selected to widen the field of view, thereby increasing the area over which the laser spots can be scanned at a time accordingly. Specifically, the use of an objective lens 6 with a lower magnification factor allows a wider area to be measured at a high speed. For example, if objective lenses having magnification factors of 20 and 4 are respectively used for the main and pre-measurement, the measurable area of the pre-measurement is 25 times greater than that of the main measurement. Therefore, the area measured during the pre-measurement is 25 times wider, which means that the measuring speed is 25 times higher.

High speed measurement can be achieved without selecting an objective lens 6 having a low magnification factor by increasing the amplitude of rough scanning with the galvano-meter 3 and by increasing the moving speed of the scanning stage 17 or by increasing the rough scanning speed along with the moving speed of the scanning speed 17, as shown in FIG. 6. If a low magnification objective lens is used in this state, measurement at a higher speed can be achieved.

Such high speed scanning over a wider range as described above will be referred to as "rough scan".

The determination of measurement conditions (step 303) is carried out according to statistic data of a cell population over a wide area obtained as described above to automatically determine measurement conditions in conformity to certain conditions.

With the scanning cytometer of the present embodiment described above, statistic data of a cell population across a wide range required for determining measurement conditions can be acquired in a short period of time, and operations to determine the validity of the measurement conditions and setting such conditions can be reduced by using such data.

(Second Embodiment)

A scanning cytometer according to a second embodiment of the present invention will now be described with reference to the accompanying drawings. Since the scanning cytometer of the present embodiment is similar to that of the first embodiment illustrated in FIGS. 3 and 4 in mechanical, optical and electrical configurations, the same parts are indicated by the same reference numbers and will not be shown and described here.

The measurement conditions of the scanning cytometer of the present embodiment are control voltages of the detectors. The detector control voltages include the application voltage and the offset adjusting voltage of the PMT and the gain and the offset of the PD. Although the description will proceed on an assumption that the detector control voltages are the application voltage and the offset adjusting voltage of the PMT, the description will equally apply to the case of the gain and the offset of the PD.

Figure 8:
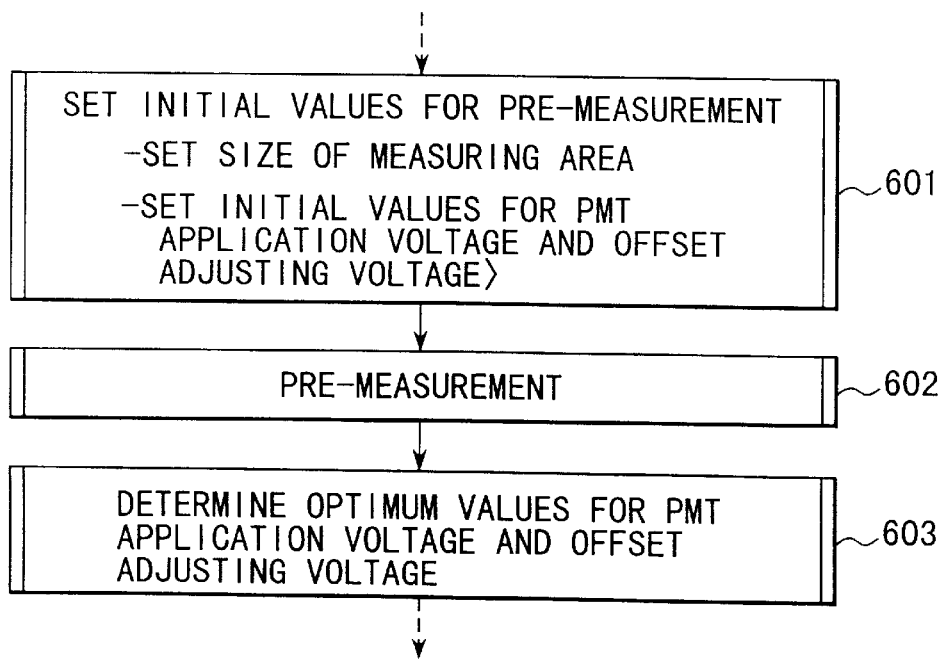
FIG. 8 is a flow chart illustrating means for setting an application voltage and an offset adjusting voltage of a PMT according to a second embodiment of the present invention.

A description will now be made with reference to FIG. 8, FIGS. 9A to 9D and FIGS. 10A and 10B on a procedure for setting control voltages of the scanning cytometer of the present embodiment as measurement conditions. As shown in FIG. 8, the setting of control voltages as measurement conditions according to the present embodiment comprises three steps, i.e., the setting of the size of the measuring area for main measurement and initial values for the application voltage and the offset adjusting voltage of the PNT (step 601), the execution of pre-measurement (step 602) and the determination of optimum values of the PMT application voltage and the offset adjusting voltage of the PMT according to statistic data acquired at the pre-measurement (step 603).

Referring first to the setting of initial values for pre-measurement, the size of the measuring area of main measurement and initial values for an application voltage HV and an offset adjusting voltage OS of the PMT are set (step 601).

First, the operator sets a desired value of the size (vertical×horizontal) of the measuring area for main measurement with the computer 22.

Next, initial values for the application voltage HV and the offset adjusting voltage OS of the PMT are set in a manner which will be described below with reference to FIGS. 9A to 9D and FIGS. 10A and 10B.

Figure 9A:
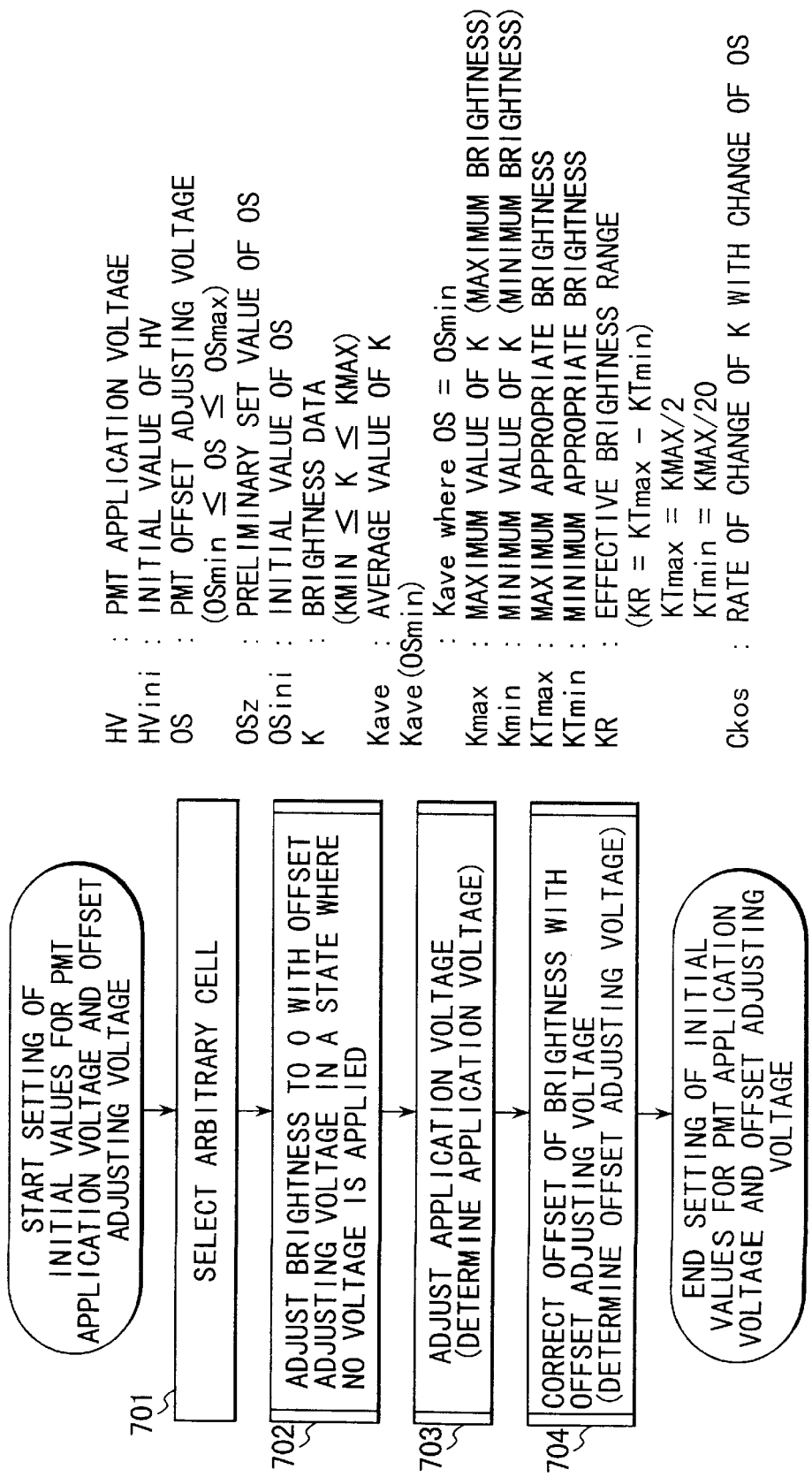
FIGS. 9A to 9D are flow charts showing steps required for determining initial values for the application voltage and the offset adjusting voltage of the PMT according to the second embodiment of the present invention.

Referring first to FIG. 9A, the operator observes the sample on the slide glass through the CCD camera 16a to select an arbitrary cell or a cell region including adjacent cells (step 701).

Next, the offset adjusting voltage OS is adjusted such that brightness is reduced to 0 in a state where no voltage is applied (HV=0) (step 702).

Figures 9B, 9C, 9D:
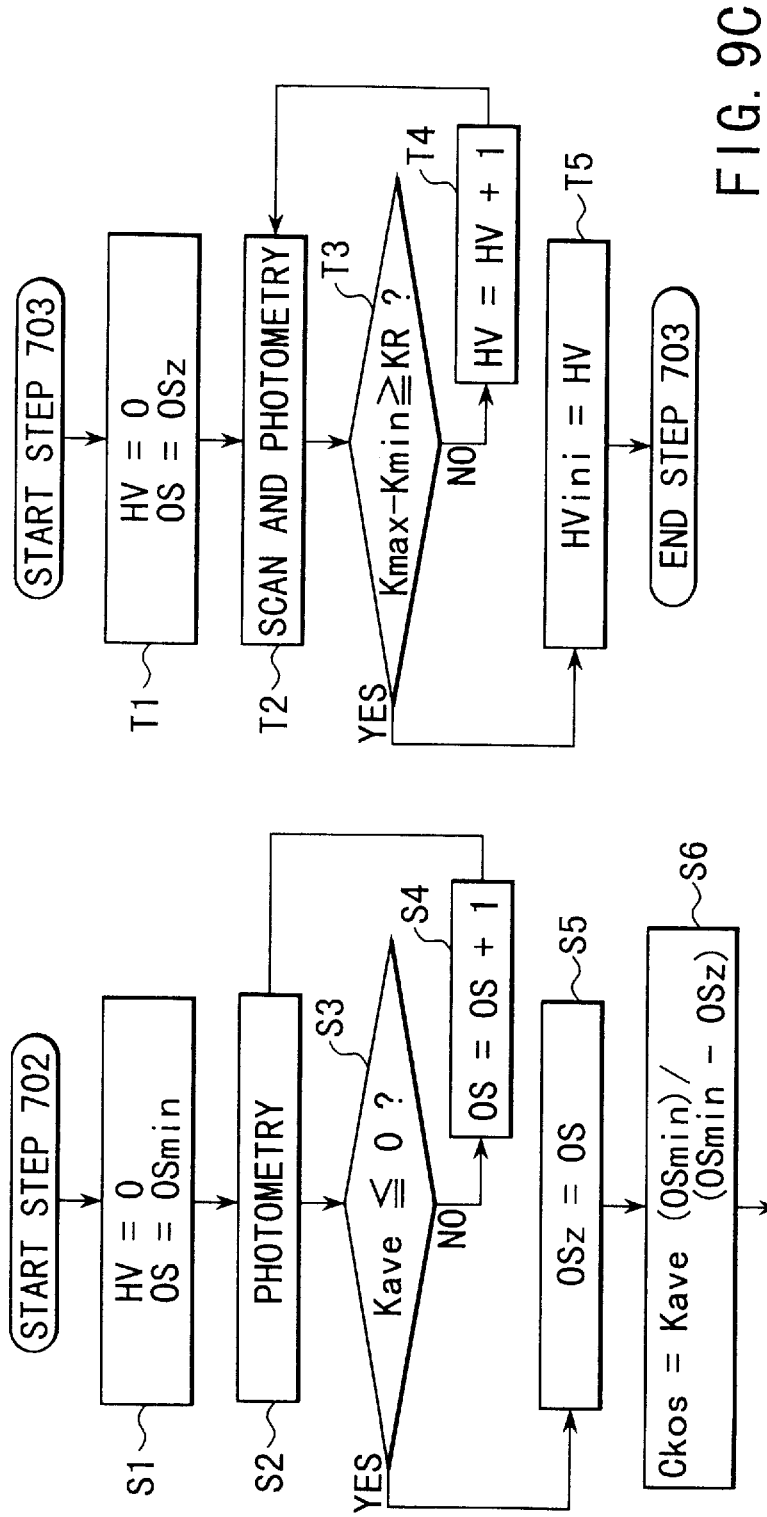

Specifically, as shown in FIG. 9B, only the offset adjusting voltage OS is varied (step S4) with the application voltage HV of the PMT 15 kept at 0 (step S1) to perform only photometry (step S2). In this case, there is no need for irradiating the sample with optical beams.

Figure 10A:
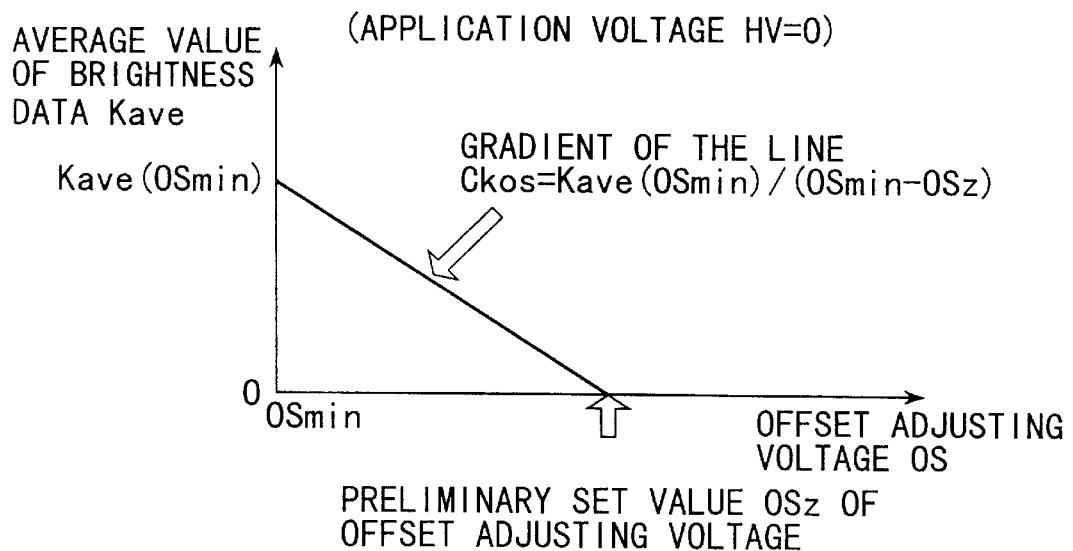
FIGS. 10A and 10B are diagrams for supplementing the explanation of the steps required for determining initial values for the application voltage and the offset adjusting voltage of the PMT according to the second embodiment of the present invention.

The result of measurement is converted by the signal processing circuits 20 into brightness data K. As shown in FIG. 10A, an offset adjusting voltage at which the average value $K_{ave}$ of the brightness data in a predetermined period of time is nearest to 0 is chosen as a preliminary set value OSz of the offset adjusting voltage (steps S3 and S5).

Although the offset adjusting voltage OS is varied here by increasing it from the minimum value $OS_{min}$ within the adjusting range thereof by increments of 1, the increment may be varied freely. Alternatively, the voltage may be decrement from the maximum value $OS_{max}$ of the measuring area, and other methods including dichotomizing search may be used.

The rate of change $Ck_{os}$ of the brightness data average value $K_{ave}$ during the transition of the offset adjusting voltage OS is calculated (step S6). Let us assume here that $K_{ave}(OS_{min})$ represents the average value of brightness data at the time when the offset adjusting voltage OS is at $OS_{min}$. Then, $Ck_{os}=K_{ave}(OS_{min})/(OS_{min}-OSz)$ This coefficient is used in the treatment of a brightness offset (step 704) to be described later.

Next, the application voltage is adjusted to determine an initial value for the application voltage (step 703).

Figure 10B:
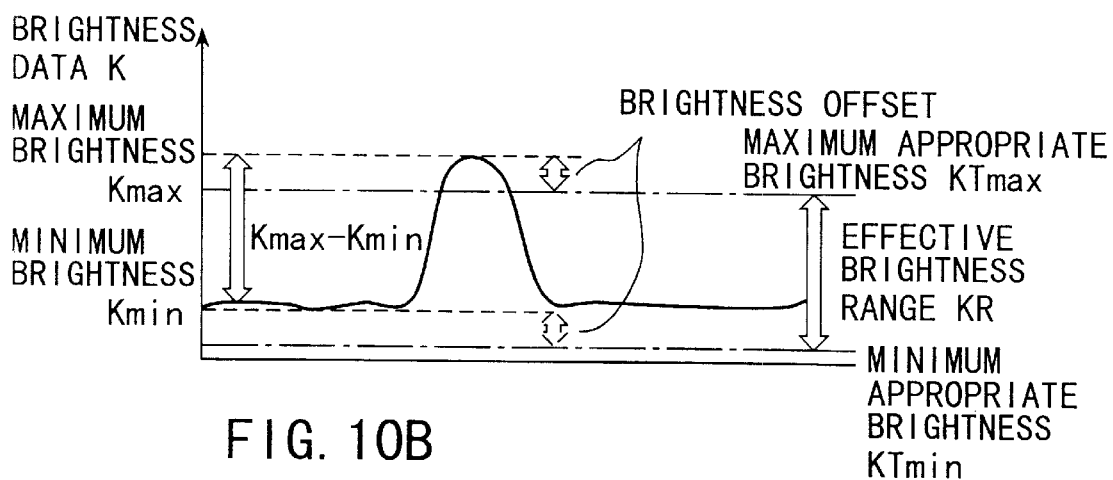
Figure 11D:
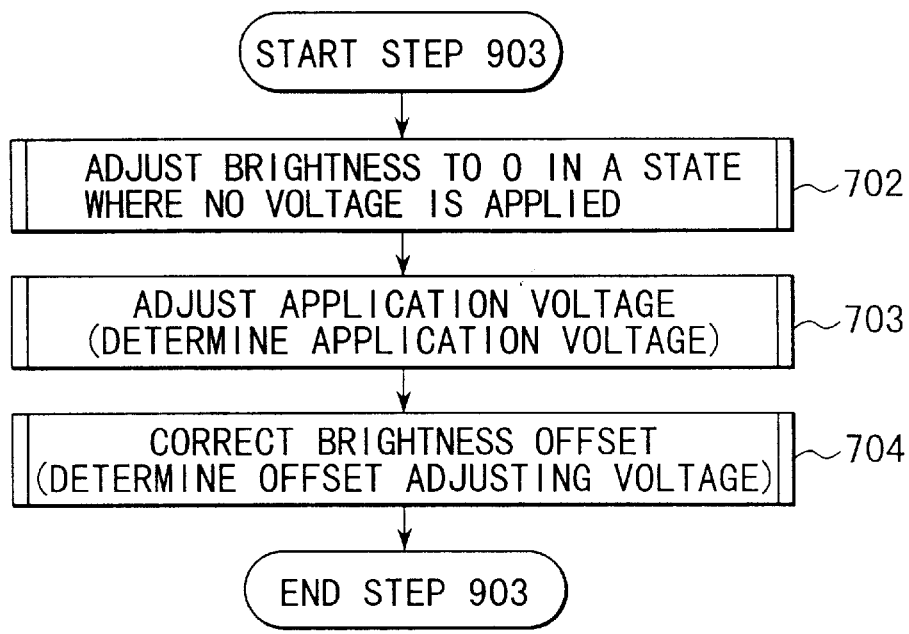

Specifically, as shown in FIG. 9C, only the application voltage HV is varied (step T4) with the offset adjusting voltage OS of the PMT 15 kept at OSz (step T1) to perform photometry by scanning optical beams across a small region including the selected cell or cell region (step T2). The result of photometry is acquired as brightness data K through the signal processing circuits 20. When the small region is one line extending across a single cell, brightness data as shown in FIG. 10B will be acquired.

An application voltage HV at which the difference ($K_{max}-K_{min}$) between the maximum value $K_{max}$ and the minimum value $K_{min}$ of the resultant brightness range KR is chosen as an initial value $HV_{ini}$ of the application voltage (steps T3 and T5).

Although the application voltage HV is increased here from 0 by increments of 1, the increment may be varied freely. Alternatively, the voltage HV may be increased or decreased from a certain value other than 0, and other methods including dichotomizing search may be used.

The small region including a cell selected here is a two-dimensional region including at least a selected cell or cell region as a whole or a one-dimensional (linear) region that laterally, longitudinally or diagonally extends through a selected cell or cell region.

As shown in FIG. 10B, an effective brightness range KR is the difference ($KT_{max}-KT_{min}$) between maximum appropriate brightness $KT_{max}$ and minimum appropriate brightness $KT_{min}$, which means that the effective area of measurement is the area between the maximum appropriate brightness $KT_{max}$ and minimum appropriate brightness $KT_{min}$ of the range of brightness. The maximum appropriate brightness $KT_{max}$ and minimum appropriate brightness $KT_{min}$ are set in advance. While they are respectively set at one half and one-twentieth of the maximum value of the brightness range (K MAX) here, those ratios may be varied freely or may be set at values desired by the operator. Further, values empirically determined depending on the type of the sample of interest may be selected.

Then, any offset in brightness attributable to the dark current of the PMT 15 and fluorescent light from the background is corrected by the offset adjusting voltage to determine an initial value for the offset adjusting voltage (step 704).

Specifically, as shown in FIG. 9D, the deviation between the maximum appropriate brightness $KT_{max}$ and the maximum brightness $K_{max}$ or the deviation between the minimum appropriate brightness $KT_{min}$ and the minimum brightness $K_{min}$ as shown in FIG. 10B is converted into an amount of offset adjusting voltage using the coefficient $Ck_{os}$ at the process of step 702, and the value is added to the preliminary set value OSz of the offset adjusting voltage as a corrective amount for the offset adjusting voltage to establish the initial value $OS_{ini}$ of the offset adjusting voltage. That is:

$$OS_{ini}=OSz+(KT_{max}-K_{max})/Ck_{os}$$

or $$OS_{ini}=OSz+(KT_{min}-K_{min})/Ck_{os} \quad (U1)$$

Next, the initial values for the application voltage and the offset adjusting voltage of the PMT thus determined are used to execute pre-measurement on a cell population as a whole distributed on the slide glass or a cell population included in an area wider than the size of the measuring area set at the process of setting the initial values for pre-measurement (step 602).

The execution of the pre-measurement will not be described here because it is similar to that in the first embodiment.

Next, optimum values for the application voltage and the offset adjusting voltage of the PMT are determined in accordance with statistic data acquired by executing the pre-measurement (step 603). The method for the determination will be described with reference to FIGS. 11A to 11D.

Referring first to FIG. 11A, cell populations or regions limited by certain conditions are extracted in accordance with the statistic data acquired at the pre-measurement (step 901).

As shown in FIG. 11B, for example, only cell populations in the process of cell division are extracted here from the statistic data acquired by executing the pre-measurement in order to discriminate cells from foreign substances and agglomerations of cells (step V1). Alternatively, as described in the third embodiment of the present invention later, regions may be extracted in which the polarization of cell distribution and the variation of fluorescent coloring is minimum. While such particular cell populations or regions may be automatically extracted by the computer 22, the operator may manually perform extraction with necessary information displayed on the monitor display 50.

Next, one cell or a plurality of cells are selected from the extracted cell populations or regions depending on conditions associated with brightness data and are moved to the measuring area using the recall function previously described (step 902).

Although one cell having the maximum brightness of fluorescent light is selected (step W1) here and is moved using the recall function (step W2) as shown in FIG. 11C, a cell A having the maximum brightness of fluorescent light and a cell B having the minimum background brightness may be selected to recall either of them.

Optimum values for the application voltage and the offset adjusting voltage of the PMT are determined from the brightness data of the one cell or the plurality of cells thus selected (step 903).

The method for determining the application voltage and the offset adjusting voltage of the PMT at this step may comprise the process of adjusting brightness to 0 in a state where no voltage is applied (step 702), the process of adjusting the application voltage (step 703) and the process of correcting brightness offset (step 704) as shown in FIG. 9D in the procedure for determining initial values for the application voltage and the offset adjusting voltage of the PMT shown in FIG. 9A.

However, when a plurality of cells are selected, e.g., a cell A having the maximum brightness of fluorescent light and a cell B having the minimum background brightness are selected and when those cells are in a positional relationship in which both of them can not be covered by a small region, the application voltage adjusting process (step 703) may be performed to vary the application voltage while moving to those cells alternately using the recall function and scanning and photometry may be performed to compare the difference between the maximum value of the brightness data of the cell A and the minimum value of the brightness data of the cell B with the effective brightness range.

An optimum value for the gain and the offset of the detectors can be determined by the above-described method.

According to the present embodiment, an optimum value for the gain and the offset of the detector can be automatically determined. It is therefore possible to reduce the time and labor which have been required for the operator to set the gain and the offset of the detectors by trial and error each time the sample 7 is changed.

Since a cell to serve as a reference to determine the gain and the offset of the detector can be selected after selecting limited cell populations or regions. in accordance with statistic data acquired at pre-measurement, it is possible, for example, to prevent the gain and the offset of the detector from being adjusted to fluorescent light emitted by foreign substances.

(Third Embodiment)

A scanning cytometer according to a third embodiment of the present invention will now be described with reference to the accompanying drawings. Since the scanning cytometer of the present embodiment is similar to that of the first embodiment illustrated in FIGS. 3 and 4 in mechanical, optical and electrical configurations, the same parts are indicated by the same reference numbers and will not be shown and described here.

In the scanning cytometer of the present embodiment, a measuring area is set as a measurement condition when measuring a sample having polarized cell distribution or variation of fluorescent coloring.

A description will now be made with reference to FIGS. 12 to 14 on a procedure for setting a measuring area for the scanning cytometer of the present embodiment as a measurement condition.

Figure 12:
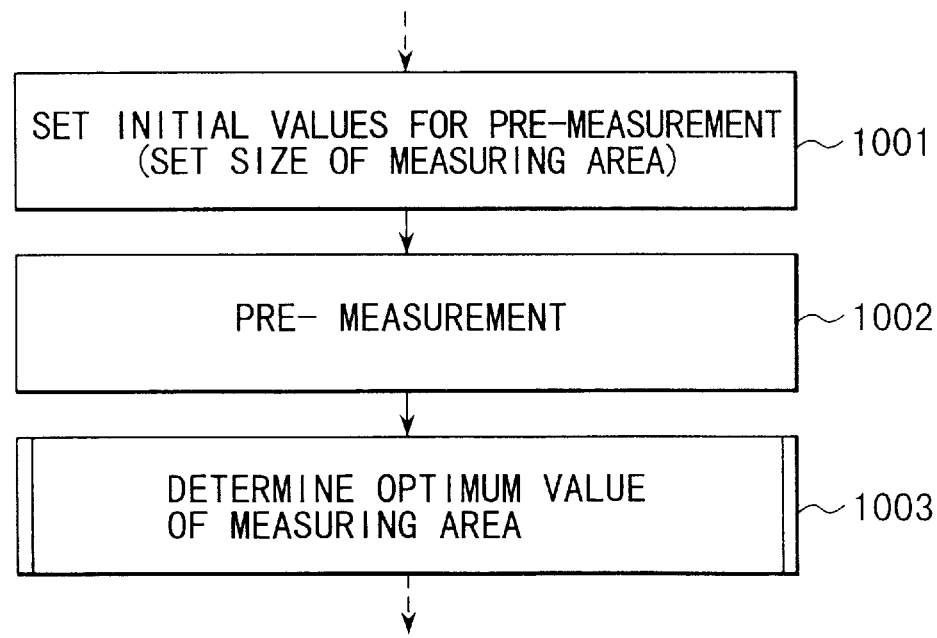
FIG. 12 is a flow chart illustrating a procedure required for setting a measuring area according to a third embodiment of the present invention.
Figure 13:
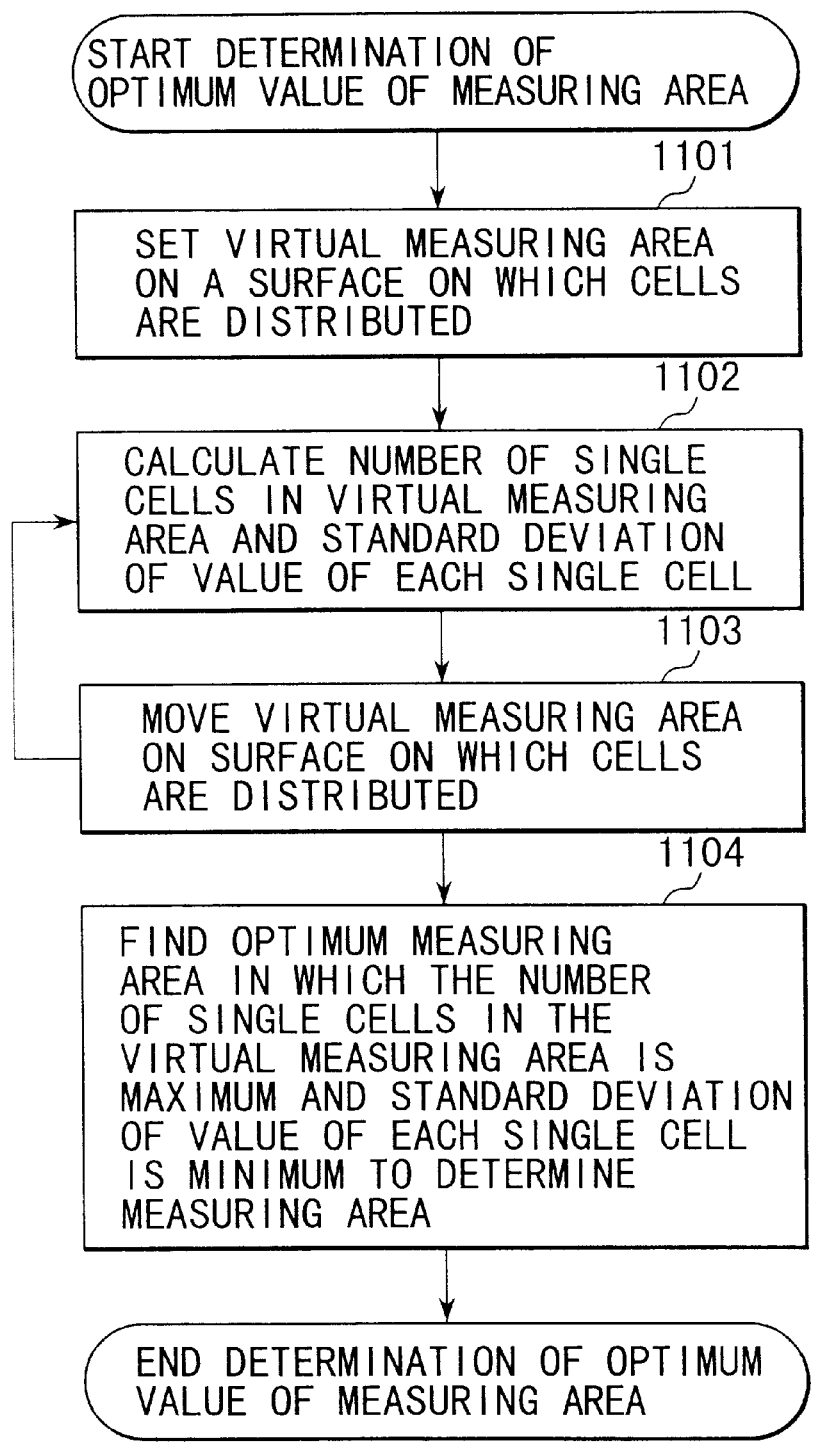
FIG. 13 is a flow chart illustrating steps required for determining an optimum value for a measuring area according to the third embodiment of the present invention.

As shown in FIG. 12, the setting of a measurement condition according to the present embodiment comprises three steps, i.e., the setting of the size (vertical and horizontal) of the measuring area (step 1001), the execution of pre-measurement (step 1002) and the determination of an optimum value for the measuring area according to statistic data acquired at the pre-measurement (step 1003).

Referring first to the setting of an initial value for the pre-measurement, a value desired by the operator is set as the size (vertical and horizontal) of the measuring area with the computer 22 (step 1001).

Next, the pre-measurement is carried out on a cell population as a whole distributed on a slide glass or a cell population included in an area wider than the measuring area set at the process of setting an initial value for the pre-measurement (step 1002).

The pre-measurement will not be described here because it is similar to that in the first embodiment described above.

Then, an optimum value for the measuring area is determined from statistic data acquired at the pre-measurement (step 1003). The method of the determination will now be described with reference to FIGS. 13 and 14.

Figure 14:
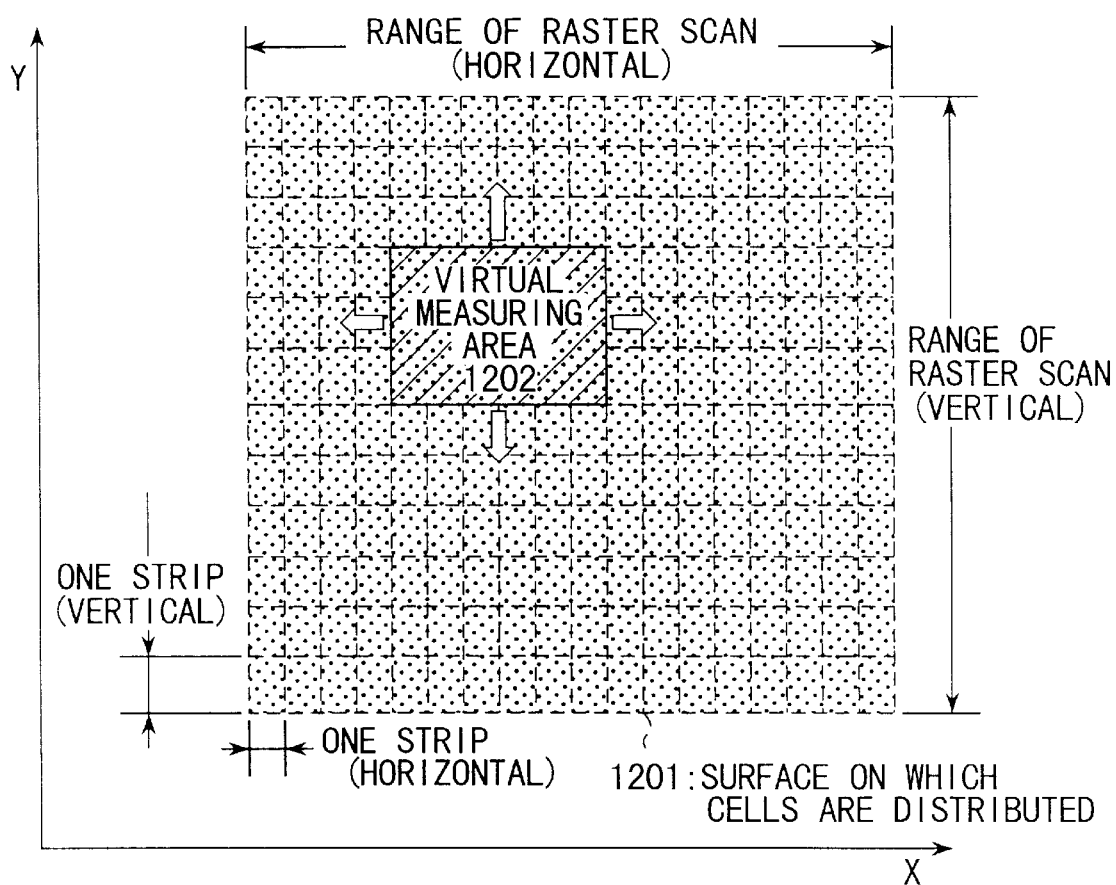
FIG. 14 illustrates a virtual measuring area on a surface on which cells are distributed according to the third embodiment of the present invention.

Referring first to FIG. 14, a virtual measuring area 1202 is set on a cell distribution surface 1201 having a distribution of cells resulting from information on the position of each cell acquired by executing the pre-measurement (step 1101). The size of the virtual measuring area 1202 is equal to the measuring area set at the step of setting an initial value for the pre-measurement.

Then, the computer 22 calculates the number of cells which are not multiple cells (single cells) included in the virtual measuring area 1202 and the standard deviation of the value of each single cell (step 1102) while the virtual measuring area 1202 is being moved on the cell distribution surface 1201 (step 1103). The width of the movement of the virtual measuring area 1202 on the cell distribution surface 1101 is equal to the interval between the strips. The width of movement may be approximately equal to the distance between nearest cells or the interval between preliminary measuring areas.

Thus, the number of single cells included in the virtual measuring area 1202 and the standard deviation of the value of each single cell are identified throughout the area measured at the pre-measurement to find an optimum measuring area in which the number of single cells is maximized and the standard deviation of the value of each cell is minimized, the optimum measuring area serving as the measuring area for the main measurement (step 1104).

Referring to the method for finding the optimum measuring area in which the number of single cells is maximized and the standard deviation of the value of each cell is minimized, the present embodiment selects a virtual measuring area, as an optimum measuring area, in which the standard deviation of the value of each cell is minimum from among virtual measuring areas in which the number of single cells is 80% or more of the maximum number. Another possible method is to select a virtual measuring area, as an optimum measuring area, in which the number of single cells is maximum from among virtual measuring areas in which the standard deviation of the value of each single cell is 120% or less of the minimum value. Obviously, the number of single cells and the level for defining the standard deviation of the value of each single cell (which is 80% or 120% in the present embodiment) may be changed.

Here, the condition for setting an optimum measuring area used here is a condition that the number of single cells is maximized and, at the same time, the standard deviation of the value of each single cell is minimized. Alternatively, a virtual measuring area in which the number of single cells is maximized may be used as the optimum measuring area. Further, a virtual measuring area in which the standard deviation of the value of each single cell is minimized may be used as the optimum measuring area.

While the computer 22 automatically searches the measuring area for the main measurement after the virtual measuring area 1202 is set on the cell distribution surface 1201 in the above description, the measuring area for the main measurement may be set by the operator who monitors information on the virtual measuring area 1202 on the cell distribution surface 1201 displayed on the monitor 50. At this time, information such as the number of cells included in the virtual measuring area and the standard deviation of the value of each cell may be calculated by the computer 22 and displayed on the monitor 50 as needed. In this case, the operator may freely change and reset the size or the position of the virtual measuring area 1202 on the computer 22.

In the present embodiment described above, the number of measurement conditions required for the operator to set can be reduced from four, i.e., the X- and Y-coordinates of the measuring starting point and coordinates of the measuring end point as described in the first embodiment to two, i.e., the width and height of the measuring area. When a sample 7 having polarized cell distribution, a cell agglomeration and variation in fluorescent coloring is measured with a conventional scanning cytometer, it takes an enormous amount of time and is actually impractical for the operator to find an optimum measuring area in which the number of single cells is maximized and the standard deviation of the value of each cell is minimized. According to the present embodiment, since the optimum measuring area can be found by automatic search using a computer, the search can be carried out with reduced labor and in a significantly reduced search time.

By setting the optimum measuring area according to the present embodiment, it is possible to improve the efficiency of cell measurement and to prevent the deterioration of the accuracy of measurement of cell cycle attributable to variation in fluorescent coloring and the like.

(Fourth Embodiment)

A scanning cytometer according to a fourth embodiment of the present invention will now be described with reference to the accompanying drawings. Since the scanning cytometer of the present embodiment is similar to that of the first embodiment illustrated in FIGS. 3 and 4 in mechanical, optical and electrical configurations, the same parts are indicated by the same reference numbers and will not be shown and described here.

In the scanning cytometer of the present embodiment, a measuring range is set as a measurement condition when measuring a sample having variation of fluorescent coloring.

A description will now be made with reference to FIGS. 15 to 17 on a procedure for setting a measuring range for the scanning cytometer of the present embodiment as a measurement condition.

Figure 15:
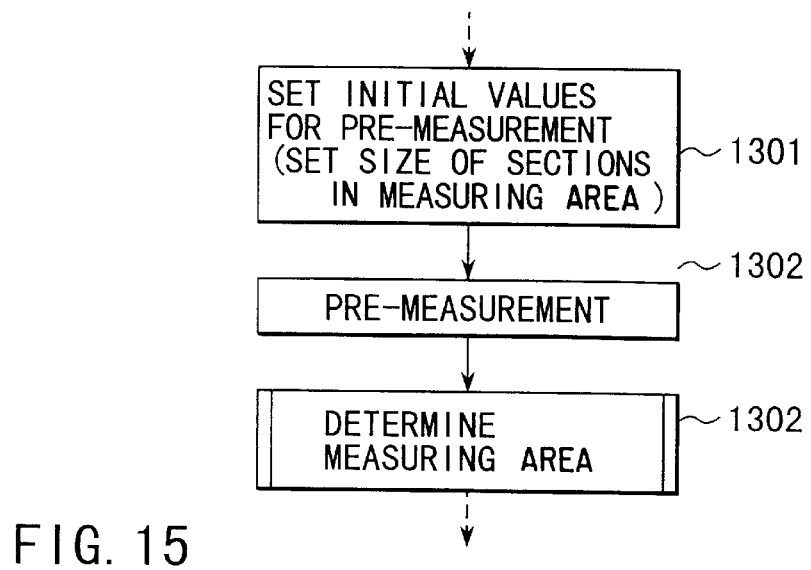
FIG. 15 is a flow chart illustrating a procedure required for setting a measuring area according to a fourth embodiment of the present invention.

As shown in FIG. 15, the setting of a measuring range as a measurement condition according to the present embodiment comprises three steps, i.e., the setting of the size of sections (step 1301), the execution of pre-measurement (step 1302) and the determination of an optimum value for the measuring range according to statistic data acquired at the pre-measurement (step 1303).

Referring first to the setting of an initial value for the pre-measurement, a value desired by the operator is set as the size of sections 1502 with the computer 22 (step 1301).

The minimum unit for scan observation is one strip because of a limitation placed by the area that can be scanned by the galvano-mirror 3 and by the size of scanned image data which can be collected at a time which is limited by the capacity of the bank memories. In such a case, the minimum size of the sections 1502 is equal to the size of one strip, and the size of the sections is specified as a multiple of the size of one strip. It is assumed here that the specified size of the sections 1502 is equal to the size of one strip. In the case of a scanning cytometer for which there is no limitation on one strip, the size of the sections 1502 is not determined by one strip and the requirement for the minimum size is only to provide statistic data for a cell population.

Next, the pre-measurement is carried out on a cell population as a whole distributed on a slide glass or a cell population included in an area wider than the size of the sections 1502 set at the step of setting an initial value for the pre-measurement (step 1302).

The pre-measurement will not be described here because it is similar to that in the first embodiment described above.

Then, an optimum value for the measuring area is determined from statistic data acquired at the pre-measurement (step 1303). The method of the determination will now be described with reference to FIGS. 16 and 17.

Figure 16:
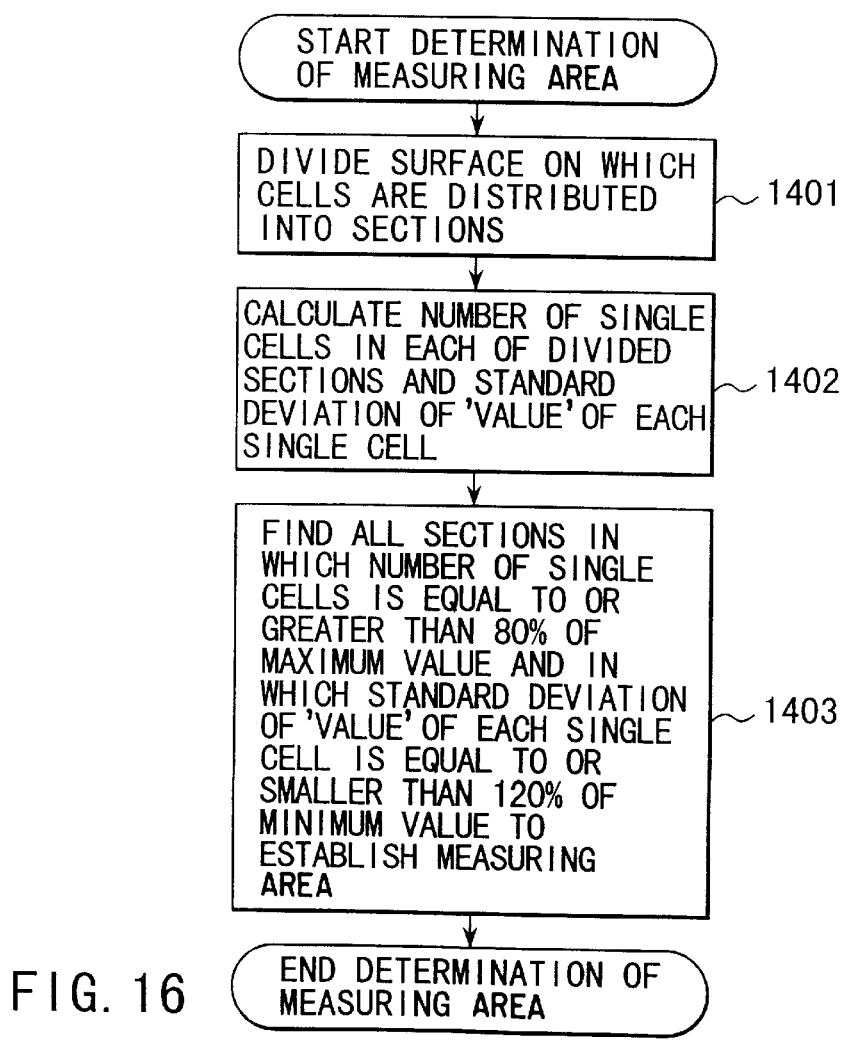
FIG. 16 is a flow chart illustrating steps required for determining a measuring area according to the fourth embodiment of the present invention.
Figure 17:
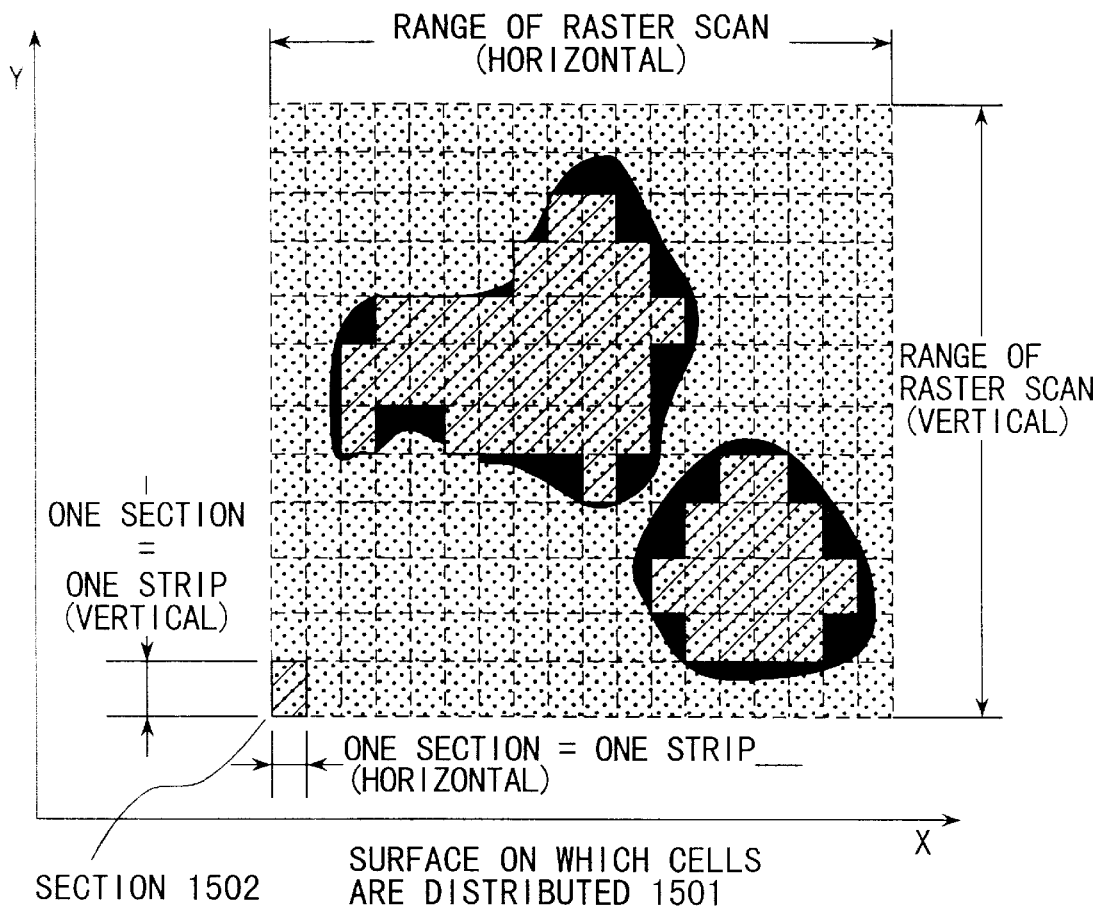
FIG. 17 is a plane view of sections on a surface on which cells are distributed according to the fourth embodiment of the present invention.

Referring first to FIG. 16, a cell distribution surface 1501 showing a distribution of cells resulting from information on the position of each cell acquired by executing the pre-measurement is divided into the sections 1502 (step 1401).

Then, the computer 22 calculates the number of single cells included in each of the section 1502 and the standard deviation of the value of each single cell (step 1402).

Thus, the number of single cells and the standard deviation of the value of each single cell are identified for all of the sections measured at the pre-measurement to find all sections in which the number of single cells is equal to or greater than a certain level and the standard deviation of the value of each cell is within a certain level, those sections serving as the measuring area for the main measurement (step 1403).

Here, all sections in which the standard deviation of the value of each single cell is 120% or less of the minimum value are chosen from among sections in which the number of single cells is 80% or more of the maximum value as the measuring area for the main measurement. Obviously, the number of single cells and the levels, e.g., 80% and 120% as described above, for defining the standard deviation of the value of each single cell may be changed.

While the computer 22 automatically searches the measuring area for the main measurement after the cell distribution surface 1501 is divided into the sections 1502, the measuring area for the main measurement may be set by the operator who monitors information on the sections 1502 on the cell distribution surface 1501 displayed on the monitor 50. At this time, information such as the number of cells included in the sections 1502 and the standard deviation of the value of each cell may be calculated by the computer 22 and displayed on the monitor 50 as needed. In this case, the operator may freely change and reset the size of the sections 1502 on the computer 22.

In the present embodiment described above, the number of measurement conditions required for the operator to set can be reduced from four, i.e., the coordinates of the measuring starting point and coordinates of the measuring end point as described in the first embodiment to one, i.e., the size of the sections (a multiple of the size of one strip). When a sample 7 having variation in fluorescent coloring is measured with a conventional scanning cytometer, it takes an enormous amount of time and is actually impractical for the operator to determine the measuring range by finding all locations where some single cells exist and where the degree of fluorescent coloring of each cell is uniform. According to the present embodiment, since the optimum measuring area can be found by automatic search using a computer, the search can be carried out with reduced labor in a significantly reduced search time.

By setting the optimum measuring area according to the present embodiment, it is possible to improve the efficiency of cell measurement and to prevent the deterioration of the accuracy of measurement of cell cycle attributable to variation in fluorescent coloring and the like.

(Fifth Embodiment)

A fifth embodiment of the present invention will now be described with reference to FIG. 18. In the above-described embodiments, control voltages for detectors or a measuring area has been determined as a measurement condition. The present embodiment is an example wherein at least one of the conditions for the detector control voltages, measuring area, contouring threshold and minimum cell area is determined prior to main measurement.

Figure 18:
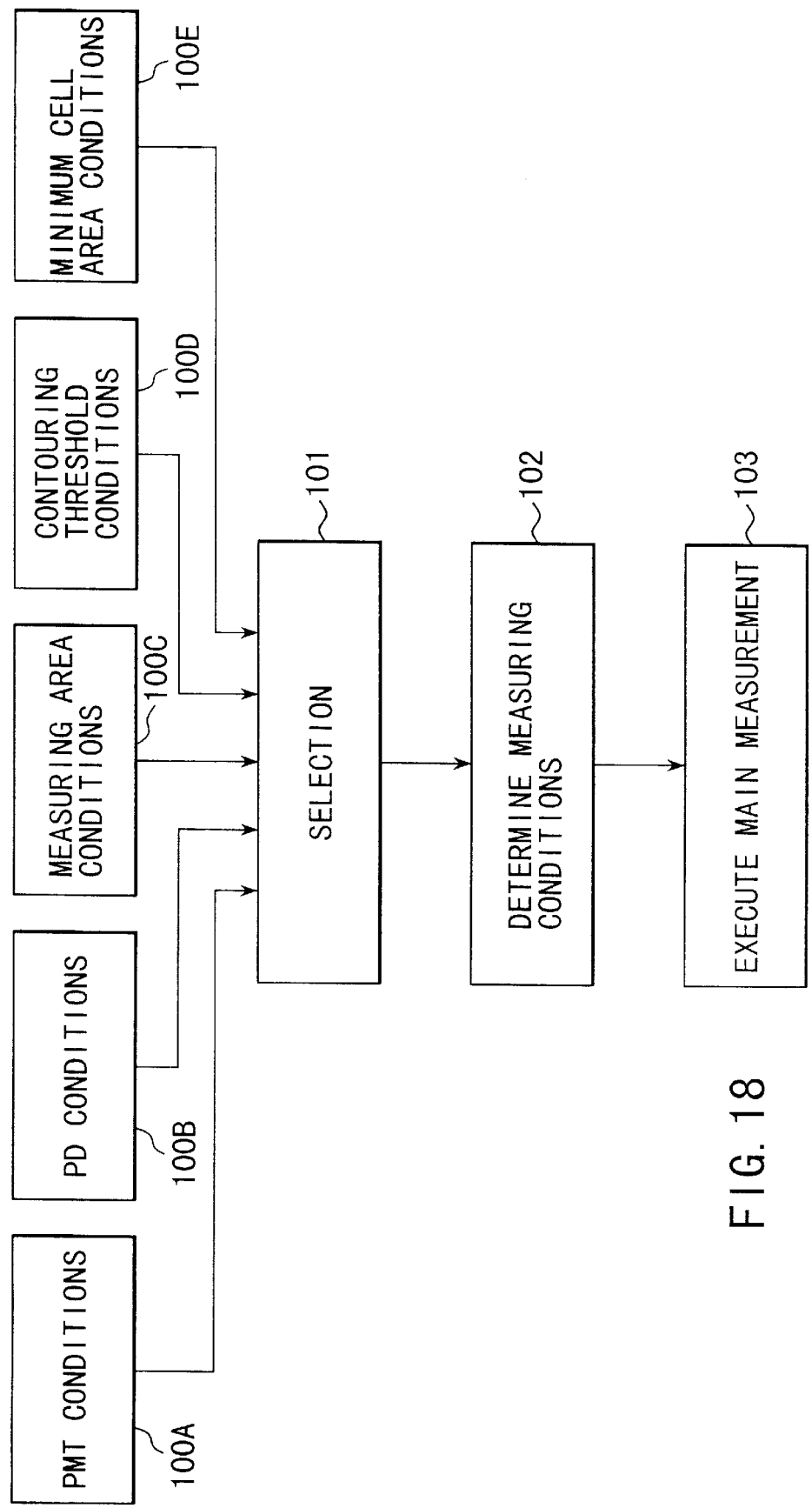
FIG. 18 is a block diagram showing major parts of an electrical configuration of a scanning cytometer according to a fifth embodiment of the present invention.

As shown in FIG. 18, at least one of a control condition of PMT 100A, a control condition of PD 100B, a measuring area condition 100C, a contouring threshold condition 100D and a minimum cell area condition 100E is selected (101). As a result, measurement conditions as conditions for main measurement are determined like the above described embodiments by scanning an area of a cell population wider than the area for the main measurement with optical beams on a two dimensional basis at a speed higher than the measuring speed of the main measurement in accordance with initial values based on one or a plurality of conditions to acquire statistic data of the cell population (102). The main measurement is executed using the determined measurement conditions.

As described above, the present invention makes it possible to provide a scanning cytometer capable of automatically setting measurement conditions such as the gain and the offset of the detector and measuring range based on data for cells in a wide range.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A scanning cytometer for scanning a cell population as a sample with optical beams in accordance with measurement conditions and for measuring light from the cells in said cell population with a detector to acquire cytometric data of said cell population, comprising:

providing means for providing main measurement in accordance with main measurement conditions as measurement conditions and pre-measurement performed prior to said main measurement in accordance with initial values for pre-measurement including measurement conditions;

setting means for setting said initial values for pre-measurement;

execution means for acquiring statistic data of said cell population by performing two-dimensional scanning of said cell population across an area wider than the area for the main measurement at a rate higher than the rate of the main measurement with optical beams in accordance with said initial values for pre-measurement set by said setting means; and determination means for determining said main measurement conditions based on the statistic data acquired by said execution means; wherein:

said measurement condition is a control condition of said detector;

said setting means comprises means for selecting at least either an arbitrary cell or cell region in said cell population after setting the size of said measuring area for the main measurement and for determining an initial value of said control voltage of the detector from brightness data of at least either said selected cell or cell region; and said determination means comprises means for selecting a certain cell in accordance with statistic data of said cell population acquired by said execution means and for determining an optimum value for the control voltage of said detector from luminance data of said selected cell.

2. A scanning cytometer according to claim 1, wherein: said detector comprises a photomultiplier for detecting fluorescent light from said cell and wherein said control condition is an application voltage of said photomultiplier.

3. A scanning cytometer according to claim 1, wherein: said detector comprises a photomultiplier for detecting fluorescent light from said cell and wherein said control condition is an offset adjusting voltage of said photomultiplier.

4. A scanning cytometer according to claim 1, wherein: said detector comprises a photodiode for detecting scattered light from said cell and wherein said control condition is a gain of said photodiode.

5. A scanning cytometer according to claim 1, wherein: said detector comprises a photodiode for detecting scattered light from said cell and wherein said control condition is an offset of said photodiode.

6. A scanning cytometer for scanning a cell population as a sample with optical beams in accordance with measurement conditions and for measuring light from the cells in said cell population with a detector to acquire cytometric data of said cell population, comprising:

providing means for providing main measurement in accordance with main measurement conditions as measurement conditions and pre-measurement performed prior to said main measurement in accordance with initial values for pre-measurement including measurement conditions;

setting means for setting said initial values for pre-measurement;

execution means for acquiring statistic data of said cell population by performing two-dimensional scanning of said cell population across an area wider than the area for the main measurement at a rate higher than the rate of the main measurement with optical beams in accordance with said initial values for pre-measurement set by said setting means; and determination means for determining said main measurement conditions based on the statistic data acquired by said execution means; and wherein:

said measurement condition is at least one of a control condition of said detector, a measuring area, a contouring threshold and a minimum cell area.

7. A scanning cytometer for scanning a cell population as a sample with optical beams in accordance with conditions for measurement and for measuring light from the cells in said cell population with a detector to acquire cytometric data of said cell population, comprising:

providing means for providing main measurement in accordance with conditions for main measurement and pre-measurement performed prior to said main measurement in accordance with conditions for pre-measurement;

setting means for setting at least one of conditions for a control condition of said detector, a measuring area, a contouring threshold and a minimum cell area;

execution means for acquiring statistic data of said cell population by performing two-dimensional scanning of said cell population across an area wider than the area for the main measurement at a speed higher than the speed of the main measurement with optical beams in accordance with initial values based on said conditions set by said setting means; and determination means for determining said conditions for main measurement based on the statistic data acquired by said execution means.

* * * * *